US009597022B2

(12) United States Patent
Addison et al.

(10) Patent No.: US 9,597,022 B2
(45) Date of Patent: Mar. 21, 2017

(54) VENOUS OXYGEN SATURATION SYSTEMS AND METHODS

(75) Inventors: Paul Addison, Edinburgh Midlothian (GB); James Watson, Fife (GB); James Ochs, Seattle, WA (US); Scott McGonigle, Edinburgh (GB)

(73) Assignee: Nellcor Puritan Bennett Ireland, Mervue (IE)

( * ) Notice: Subject to any disclaimer, the term of this patent is extended or adjusted under 35 U.S.C. 154(b) by 1320 days.

(21) Appl. No.: 13/229,458

(22) Filed: Sep. 9, 2011

(65) Prior Publication Data

US 2013/0066174 A1 Mar. 14, 2013

(51) Int. Cl.
*A61B 5/1455* (2006.01)
*A61B 5/00* (2006.01)

(52) U.S. Cl.
CPC .......... *A61B 5/14551* (2013.01); *A61B 5/726* (2013.01); *A61B 5/7207* (2013.01); *A61B 5/7239* (2013.01)

(58) Field of Classification Search
USPC ................................................ 600/310–344
See application file for complete search history.

(56) References Cited

U.S. PATENT DOCUMENTS

| | | | |
|---|---|---|---|
| 4,289,141 A | 9/1981 | Cormier | |
| 5,253,646 A * | 10/1993 | Delpy et al. | 600/310 |
| 5,439,483 A | 8/1995 | Duong-Van | |
| 5,590,650 A | 1/1997 | Genova | |
| 5,632,272 A | 5/1997 | Diab et al. | |
| 5,778,881 A | 7/1998 | Sun et al. | |
| 5,795,304 A | 8/1998 | Sun et al. | |
| 5,797,840 A | 8/1998 | Akselrod | |
| 5,827,195 A | 10/1998 | Lander | |
| 5,967,995 A | 10/1999 | Shusterman et al. | |
| 6,002,952 A | 12/1999 | Diab et al. | |
| 6,036,653 A | 3/2000 | Baba et al. | |

(Continued)

FOREIGN PATENT DOCUMENTS

| | | |
|---|---|---|
| JP | 09-084776 A | 3/1997 |
| WO | 0125802 A2 | 4/2001 |

(Continued)

OTHER PUBLICATIONS

Lynch J. and Kaemmerer, H., "Comparison of a Modified Fick Method with Thermodilution for Determining Cardiac Output in Critically ill Patients on Mechanical Ventilation," Intensive Care Medicine, vol. 16, No. 4, Apr. 1990, pp. 248-251.

(Continued)

*Primary Examiner* — Tse Chen
*Assistant Examiner* — Marjan Fardanesh

(57) ABSTRACT

Methods and systems are discussed for determining venous oxygen saturation by calculating a ratio of ratios from respiration-induced baseline modulations. A calculated venous ratio of ratios may be compared with a look-up table value to estimate venous oxygen saturation. A calculated venous ratio of ratios is compared with an arterial ratio of ratios to determine whether baseline modulations are the result of a subject's respiration or movement. Such a determination is also made by deriving a venous ratio of ratios using a transform technique, such as a continuous wavelet transform. Derived venous and arterial saturation values are used to non-invasively determine a cardiac output of the subject.

17 Claims, 24 Drawing Sheets

(56) References Cited

U.S. PATENT DOCUMENTS

| | | |
|---|---|---|
| 6,094,592 A | 7/2000 | Yorkey |
| 6,095,984 A | 8/2000 | Amano et al. |
| 6,117,075 A | 9/2000 | Barnea |
| 6,129,675 A | 10/2000 | Jay |
| 6,135,966 A | 10/2000 | Ko |
| 6,171,257 B1 | 1/2001 | Weil et al. |
| 6,171,258 B1 | 1/2001 | Karakasoglu et al. |
| 6,208,951 B1 | 3/2001 | Kumar et al. |
| 6,293,915 B1 | 9/2001 | Amano et al. |
| 6,325,761 B1 | 12/2001 | Jay |
| 6,361,501 B1 | 3/2002 | Amano et al. |
| 6,393,311 B1 | 5/2002 | Edgar, Jr. et al. |
| 6,561,986 B2 | 5/2003 | Baura |
| 6,608,934 B2 | 8/2003 | Scheirer |
| 6,654,623 B1 | 11/2003 | Kastle |
| 6,810,277 B2 | 10/2004 | Edgar, Jr. et al. |
| 6,931,269 B2 | 8/2005 | Terry |
| 6,985,763 B2 | 1/2006 | Boas et al. |
| 6,993,377 B2 | 1/2006 | Flick |
| 7,001,337 B2 | 2/2006 | Dekker |
| 7,020,507 B2 | 3/2006 | Scharf |
| 7,035,679 B2 | 4/2006 | Addison |
| 7,043,293 B1 | 5/2006 | Baura |
| 7,054,453 B2 | 5/2006 | Causevic |
| 7,054,454 B2 | 5/2006 | Causevic et al. |
| 7,079,888 B2 | 7/2006 | Oung |
| 7,171,269 B1 | 1/2007 | Addison |
| 7,173,525 B2 | 2/2007 | Albert |
| 7,203,267 B2 | 4/2007 | De Man et al. |
| 7,225,013 B2 | 5/2007 | Geva et al. |
| 7,254,500 B2 | 8/2007 | Makeig |
| 7,289,835 B2 | 10/2007 | Mansfield |
| 7,477,571 B2 | 1/2009 | Melese |
| 7,515,949 B2 | 4/2009 | Norris |
| 7,519,488 B2 | 4/2009 | Fu |
| 7,523,011 B2 | 4/2009 | Akiyama et al. |
| 7,566,306 B2 | 7/2009 | Fujiwara et al. |
| 7,613,507 B2 | 11/2009 | Vitali et al. |
| 7,725,146 B2 | 5/2010 | Li et al. |
| 7,725,147 B2 | 5/2010 | Li et al. |
| 7,811,234 B2 | 10/2010 | McGrath |
| 7,819,812 B2 | 10/2010 | John et al. |
| 7,922,665 B2 | 4/2011 | Baker |
| 7,944,551 B2 | 5/2011 | Addison et al. |
| 7,951,129 B2 | 5/2011 | Chinchoy |
| 2004/0260186 A1 | 12/2004 | Dekker |
| 2006/0211930 A1 | 9/2006 | Scharf et al. |
| 2006/0258921 A1 | 11/2006 | Addison et al. |
| 2007/0021673 A1 | 1/2007 | Arbel et al. |
| 2007/0167694 A1 | 7/2007 | Causevic et al. |
| 2007/0276210 A1 | 11/2007 | Gutierrez |
| 2007/0282212 A1 | 12/2007 | Sierra et al. |
| 2008/0082018 A1 | 4/2008 | Sackner et al. |
| 2008/0214903 A1 | 9/2008 | Orbach |
| 2008/0243021 A1 | 10/2008 | Causevic et al. |
| 2009/0324034 A1 | 12/2009 | Watson et al. |
| 2009/0326395 A1 | 12/2009 | Watson et al. |
| 2010/0014723 A1* | 1/2010 | Addison et al. ............. 382/128 |
| 2010/0152591 A1 | 6/2010 | Yu et al. |
| 2010/0298728 A1* | 11/2010 | Addison et al. ............. 600/504 |
| 2011/0028802 A1* | 2/2011 | Addison et al. ............. 600/301 |
| 2011/0112379 A1* | 5/2011 | Li et al. ....................... 600/300 |
| 2011/0112387 A1 | 5/2011 | Li et al. |

FOREIGN PATENT DOCUMENTS

| | | |
|---|---|---|
| WO | 0162152 A1 | 8/2001 |
| WO | 03055395 A1 | 7/2003 |
| WO | 2004105601 A1 | 12/2004 |
| WO | 2005096170 | 10/2005 |
| WO | 2006085120 A1 | 8/2006 |

OTHER PUBLICATIONS

Mahutte C.K., Jaffe M.B., Sassoon C.S., and Wong D.H. "Cardiac output from carbon dioxide production and arterial and venous oximetry," Crit. Care Med., vol. 19, No. 10, Oct. 1991, pp. 1270-1277.

Addison, Paul S., The Illustrated Wavelet Transform Handbook, Taylor & Francis Group, 2002, pp. 1-353.

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, vol. 21, No. 1, 2007, pp. 55-61.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, vol. 20, No. 1. 2006, pp. 33-36.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

Walton, Z. D., Kyriacou, P.A., Silverman, D.G., and Shelly, K.H. "Measuring Venous Oxygenation Using The Photoplethysmograph Waveform," Journal of Clinical Monitoring and Computing, vol. 24, 2010, pp. 295-303.

U.S. Appl. No. 13/229,490, filed Sep. 9, 2011.
U.S. Appl. No. 13/229,476, filed Sep. 9, 2011.
U.S. Appl. No. 13/229,465, filed Sep. 9, 2011.

* cited by examiner

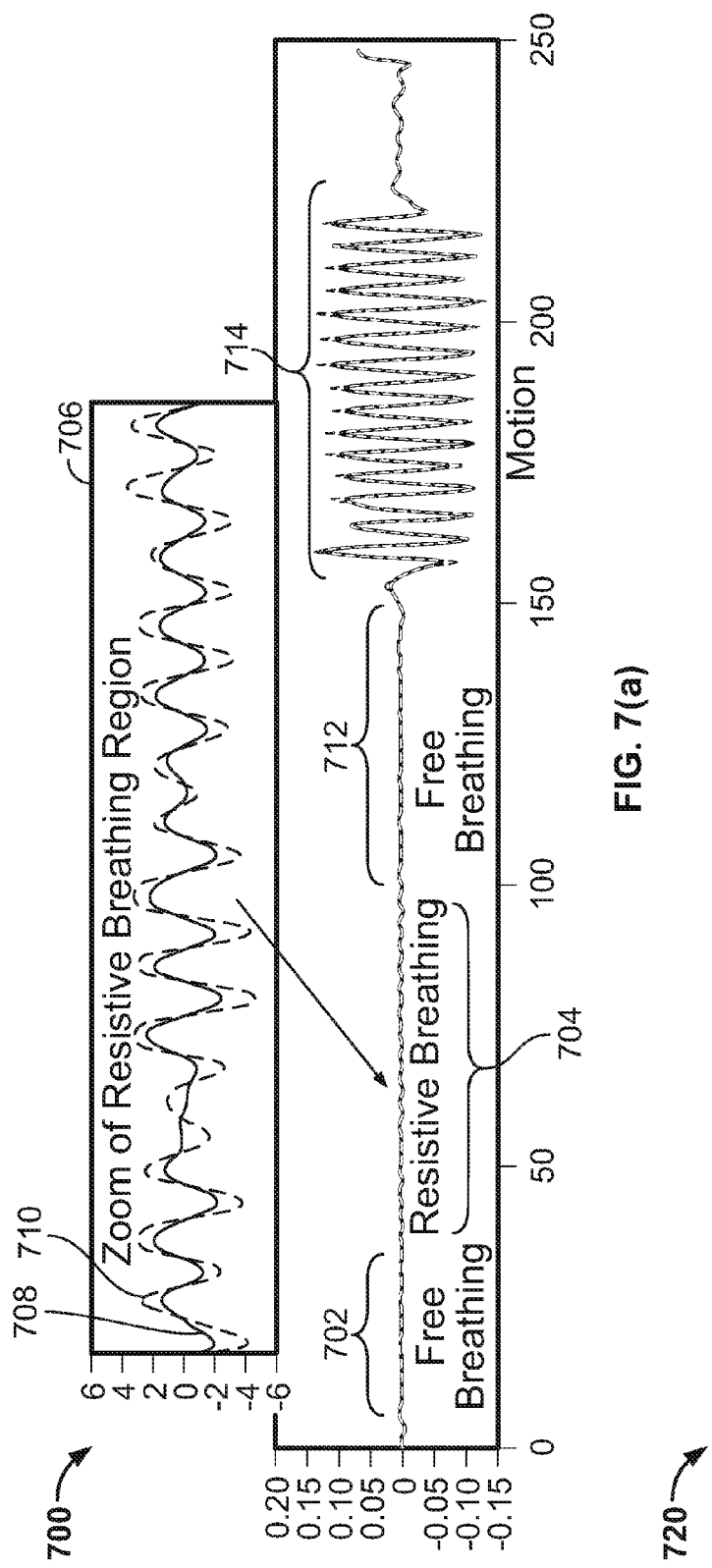
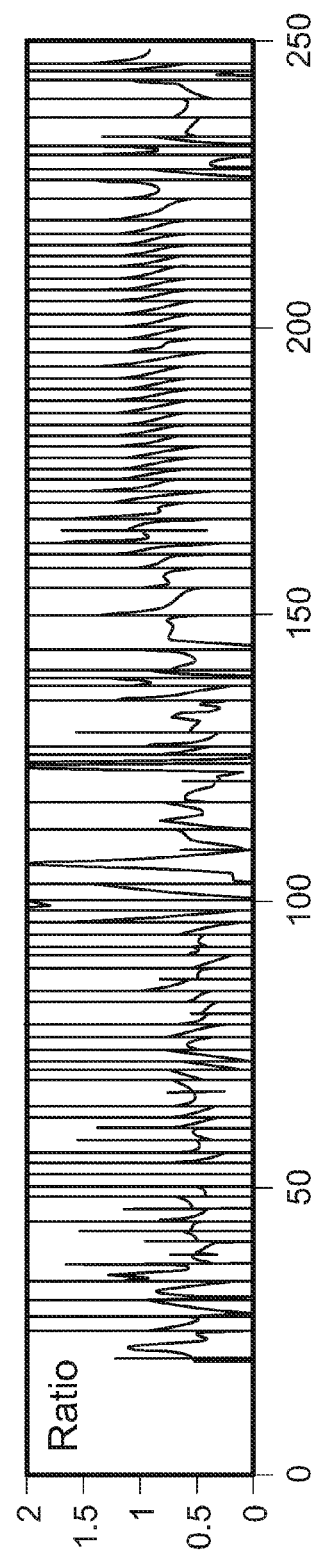
FIG. 7(a)
FIG. 7(b)

VENOUS OXYGEN SATURATION SYSTEMS AND METHODS

SUMMARY

The present disclosure relates to signal processing and analysis and, more particularly, the present disclosure relates to systems and methods for calculating and utilizing values related to venous oxygen saturation.

In conventional pulse oximetry, a subject's arterial oxygen saturation is estimated from a ratio of ratios calculated from the amplitude of cardiac pulsatile components of red and infrared signals. In the present disclosure, methods and systems are provided for estimating a subject's venous oxygen saturation by calculating a ratio of ratios from the amplitude of respiratory modulations that have been obtained from the subject's pulse oximetry signal, such as photoplethysmographic ("PPG") signal obtained from one or more sensing devices. Methods and systems are also provided for using the ratio of ratios based on respiration modulations to analyze the quality of the subject's PPG signal and to identify features of the subject's physiological condition, such as venous blood oxygen saturation and cardiac output.

In certain aspects, a ratio of ratios calculated based on respiration modulations is compared to a calculated ratio of ratios based on cardiac pulsatile components to determine signal quality. For example, a signal quality metric may indicate the extent to which motion artifact may be interfering with the detection of respiratory modulations or cardiac pulses. This signal quality metric may also be used to determine a confidence level for calculated arterial or venous oxygen saturation values. A signal quality metric may also be calculated by computing the wavelet transform of a physiological signal and examining one or more regions of interest on a ratio surface derived from the transform. Based in part on these signal quality metrics, signal processing algorithms may adjust their function to compensate for motion artifact, appropriately weight any calculated values, decide that it is not possible to calculate sufficiently accurate values, activate an alarm, or take any other appropriate action.

The present disclosure provides methods and systems for calculating a ratio of ratios from respiratory modulation signals. The calculated ratio of ratios may be compared with values in a look-up table to derive a venous oxygen saturation value. The calculated ratio of ratios may alternatively be mapped to venous oxygen saturation values. Such a mapping may be derived empirically. Such estimates of venous oxygen saturation are particularly relevant to subjects who use ventilators. Because estimating venous oxygen saturation, unlike estimating arterial oxygen saturation, does not require obtaining a physiological signal from a part of the body, such as a finger or toe, with a strong cardiac pulsatile component, alternative sites for obtaining physiological signals may be used, such as a subject's chest wall or deeper regions of the body. Once a venous oxygen saturation value is estimated from a signal of sufficient quality, the venous oxygen saturation value may be used with a derived arterial oxygen saturation value to determine a patient's cardiac output non-invasively using Fick's equation or any other applicable method.

In certain embodiments, methods are provided for determining a subject's physiological condition by obtaining a first PPG signal from the subject, based on light transmission at a first wavelength, and using that signal to determine data indicative of the oxygen saturation of the subject's blood. In particular, a pulsatile component is removed from the first signal to create a first filtered signal indicative of a first baseline modulation. A second PPG signal is also obtained from the subject, based on light transmission at a second wavelength, and a pulsatile component is removed from the second signal to create a second filtered signal indicative of a second baseline modulation. A first ratio is determined by dividing an amplitude of the first filtered signal by a first numeric component. A second ratio is determined by dividing an amplitude of the second filtered signal by a second numeric component. The first ratio is divided by the second ratio to create a ratio of ratios indicative of the subject's physiological condition.

In some embodiments, the first numeric component is a modified amplitude of the first baseline modulation. In some embodiments, the second numeric component is a modified amplitude of the second baseline modulation. In some embodiments, the first numeric component is a mean baseline value of the first baseline modulation, and the second numeric component is a mean baseline value of the second baseline modulation. A first logarithm of the first ratio and a second logarithm of the second ratio may be calculated. In certain embodiments, the step of dividing the first ratio by the second ratio is performed by dividing the first logarithm by the second logarithm to create the ratio of ratios.

A venous oxygen saturation may be determined based on the ratio of ratios. In some embodiments, determining venous oxygen saturation includes comparing the ratio of ratios to a value in a look-up table. The look-up table may include a set of venous oxygen saturation values, each value in the set of venous oxygen saturation values being associated with a corresponding value of the physiological venous oxygen saturation. In some embodiments, determining venous oxygen saturation includes mapping the ratio of ratios to venous oxygen saturation values. Such a mapping may be derived empirically.

In some embodiments, the filtering is coordinated with a respiration rate of a ventilator. In some embodiments, arterial oxygen saturation is determined simultaneously with the venous oxygen saturation using the removed pulsatile components. The arterial oxygen saturation may be determined using $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)},$$

where $\beta o$ and $\beta r$ are empirically derived absorption coefficients, $\lambda_R$ and $\lambda_{IR}$ are wavelengths, R is the ratio of ratios, and s is the arterial oxygen saturation.

In some embodiments, the first PPG signal and the second PPG signal are obtained non-invasively.

Systems are also provided for deriving the subject's venous oxygen saturation or other physiological information, the subject's pulse oximetry signal, which has pulsatile components indicative of light transmission by arterial blood in the subject, and baseline components indicative of light transmission by venous blood in the subject. The systems include a filter that removes the pulsatile components from the pulse oximetry signal to create a filtered signal and a signal processor programmed to identify within the filtered signal a first amplitude indicative of a baseline component from a red light source and a second amplitude indicative of a baseline component from an infrared light source. The signal processor is programmed to determine a first ratio that includes the first amplitude divided by a mean of a plurality of amplitudes from the red light source and a second ratio that includes the second amplitude divided by a mean of a plurality of amplitudes from the infrared light source. The signal processor is also programmed to divide the first and second ratios to create a modified signal. In some embodiments, the signal processor is further configured to determine venous oxygen saturation based on the modified signal.

In some embodiments, the filter removes the pulsatile components by filtering around a respiration rate of a ventilator. In some embodiments, the signal processor is further configured to determine arterial oxygen saturation simultaneously using ratio-of-ratios calculation involving the filtered pulsatile components. In some embodiments, a venous component represents modulation of light transmission corresponding to venous blood in the subject. In some embodiments, the pulse oximetry signal is obtained non-invasively. In some embodiments, the signal processor is further configured to extract the venous component and the baseline components indicative of light transmission by venous blood in the subject by filtering the pulse oximetry signal.

Methods and systems are also provided for using the ratio of ratios, corresponding to venous blood, to perform one or more analyses on the signal to assess the source and quality of the signal. For example, a calculated ratio of ratios based on respiration modulations may be used to determine the extent to which motion is interfering with the detection of respiratory modulations and the confidence in any calculated values. A ratio of ratios of unity may be an indication of movement artifact. Also, if an obtained physiological signal includes both a cardiac pulsatile component and a secondary modulation component, a calculated ratio of ratios based on the secondary modulation component that is similar to a calculated ratio of ratios based on the cardiac pulse component may be a positive indication that the secondary modulations are due to respiration. The methods include, for example, calculating, from the obtained physiological signal, a first ratio value indicative of a secondary modulation in the obtained physiological signal and obtaining a second ratio value indicative of a pulsatile component in the obtained physiological signal. In certain implementations, if the first ratio value and the second ratio value are very similar and neither are near unity, this may indicate that the secondary modulations in the signal are more likely caused by respiration than movement.

In some embodiments, systems are provided for analyzing a physiological signal obtained from a subject, which include a signal input configured to receive the physiological signal of the subject from a sensing device. The systems also include one or more processing devices in communication with the signal input and configured to calculate, from the physiological signal, a first ratio value indicative of a respiration modulation in the physiological signal. The one or more processing devices are configured to calculate, from the physiological signal, a second ratio value indicative of a pulsatile component in the physiological signal. The one or more processing devices are also configured to provide an indication of the first ratio value relative to the second ratio value, which may be used to determine at least one of the quality of the obtained signal and whether modulations in the signal are due to respiration or movement.

In some embodiments, the indication of the first ratio value relative to the second ratio value includes an indication of a difference between a threshold value and a combined ratio of ratios, which may indicate whether modulations in the signal are due to respiration or motion of the subject. The combined ratio of ratios includes a function of the first ratio of ratios and the second ratio of ratios. In some embodiments, the threshold value is derived from a long-term difference between respiration and pulsatile modulations in data collected from the subject over time, which indicates oxygen demand at a part of the subject's body (e.g. finger tip).

In some embodiments, the systems include an indicator for indicating whether baseline modulation in a signal component is due to respiration or motion of the subject. The indicator may indicate that a baseline modulation in at least one of first and second wavelength components taken from the subject is due to respiration of the subject when there are small deviations of the combined ratio of ratios from a threshold value. The indicator may indicate that a baseline modulation in at least one of the first and second wavelength components is due to motion of the subject when there are large deviations of the combined ratio of ratios from the threshold value. The indicator may include an alarm that is triggered when a baseline modulation in at least one of the first and second wavelength components is due to motion of the subject.

In certain implementations, the signal quality of an obtained physiological signal may be tested by transforming physiological signals. In some embodiments, methods are provided that include transforming a first physiological signal based on light transmission at a first wavelength to generate a first transformed signal. The methods include transforming a second physiological signal based on light transmission at a second wavelength to generate a second transformed signal. A ratio surface is derived from the first transformed signal and the second transformed signal, and a first region of interest on the ratio surface indicative of venous perturbation is identified, which may be related to a respiration rate of the subject. A representative value is calculated for the first region of interest on the ratio surface. Based on the calculated representative value, the quality of the signals may be evaluated by determining whether the representative value for the first region of interest indicates respiration or motion of the subject.

In some embodiments, deriving the ratio surface involves normalizing the first and second physiological signals by a value, for example dividing the respective magnitude of each of the first and second physiological signals by the respective minimum, maximum, mean, DC component, or standard deviation computed over a time window of the first and second physiological signals.

In some embodiments, transforming the first and second signal includes using a wavelet transform. In some embodiments, the wavelet transform is applied to derivatives of the first and second signals.

In some embodiments, determining whether the representative value for the first region of interest indicates respiration or motion of the subject involves identifying a second region of interest on the ratio surface related to a cardiac pulse frequency. A representative value is calculated for the second region of interest, and the representative value for the first region of interest is compared with the representative value for the second region of interest. The representative values for the first and second regions of interest may correspond to respective first and second functions. Comparing the representative value for the first region of interest with the representative value for the second region of interest may include, for example, comparing corresponding points on the first and second functions, respective median values of the first and second functions, respective average values of the first and second functions, or corresponding portions of the first and second functions. Similar representative values for the first and second regions of interest that are not near unity are indicative of baseline modulations in the first and second signals being more likely caused by respiration than movement.

In some embodiments, systems provide one or more processing devices that transform a first physiological signal based on light transmission at a first wavelength to generate a first transformed signal. The one or more processing devices may also be configured to transform a second physiological signal based on light transmission at a second wavelength to generate a second transformed signal. One or more processing devices are configured to derive a ratio surface from the first transformed signal and the second transformed signal and to calculate a representative value for a first region of interest on the ratio surface, which may be related to a respiration rate of the subject. The calculated representative value may indicate whether baseline modulation in at least one of the first and second signals is due to respiration of the subject.

In some embodiments, the one or more processing devices are configured to transform the first and second signal using a wavelet transform. In some embodiments, the one or more processing devices are configured to calculate a first modulus of the transform of the first signal, calculate a second modulus of the transform of the second signal, and divide the first modulus by the second modulus, resulting in the ratio surface from which representative values indicative of signal quality can be derived.

Methods and systems are also provided for using venous oxygen saturation values to non-invasively assess physiological conditions of the subject. Such non-invasive methods and systems provide several advantages over invasive techniques, including minimizing the subject's pain and recovery time. In some embodiments, non-invasive methods are provided for determining cardiac information about a subject by obtaining a first non-invasive physiological signal that includes a component indicative of arterial blood in the subject and a second non-invasive physiological signal that includes a component indicative of venous blood in the subject. The venous blood may be mixed venous blood, central venous blood, or other venous blood of interest in the methods described herein. An arterial blood oxygen content is determined from the first physiological signal and a venous blood oxygen content is determined from the second physiological signal. A cardiac output is determined, for example by using Fick's equation, based at least in part on the arterial blood oxygen content and the venous blood oxygen content.

In some embodiments, the first physiological signal and second physiological signal are PPG signals. In some embodiments, an oxygen consumption rate of the subject is measured and used with the arterial and venous blood contents to calculate the cardiac output. In some embodiments, determining the cardiac output includes determining the amount of oxygen consumed by the patient, determining an arterio-venous oxygen concentration difference, and determining cardiac output as a flow rate by dividing the oxygen consumption by the concentration difference.

Computer readable media are also provided for non-invasively determining venous oxygen saturation, assessing signal quality using the respiratory modulations, and assessing physiological conditions of the subject. In some embodiments, computer readable media have stored instructions that when executed direct a first input port to receive a first non-invasive physiological signal that includes a component indicative of arterial blood, and direct a second input port to receive a second non-invasive physiological signal that includes a component indicative of venous blood return. The computer readable media direct processing equipment to determine an arterial blood oxygen content based at least in part on a first set of components derived from the first physiological signal and to determine a venous blood oxygen content based at least in part on a second set of components derived from the second physiological signal. The computer readable media also direct processing equipment to determine, for example using Fick's equation, a cardiac output based at least in part on the oxygen consumption rate, the arterial blood oxygen content, and the venous blood oxygen content.

In some embodiments, the computer readable media direct a third input port to receive a signal that measures an oxygen consumption rate of the subject, which can then be used with the arterial and venous blood contents to calculate the cardiac output. In some embodiments, processing equipment is directed to determine an arterio-venous oxygen concentration difference by subtracting the venous blood oxygen content from the arterial blood oxygen content, and to determine cardiac output as a flow rate by dividing the oxygen consumption rate by the concentration difference.

BRIEF DESCRIPTION OF THE DRAWINGS

The above and other features of the present disclosure, its nature and various advantages will be more apparent upon consideration of the following detailed description, taken in conjunction with the accompanying drawings in which:

FIG. 7(a) shows an illustrative plot of normalized respiration modulation signals derived from red and infrared PPG signals in accordance with some embodiments;

FIG. 7(b) shows an illustrative ratio signal obtained by dividing the red and infrared signals of FIG. 7(a) by each other in accordance with some embodiments;

DETAILED DESCRIPTION

Figure 1:
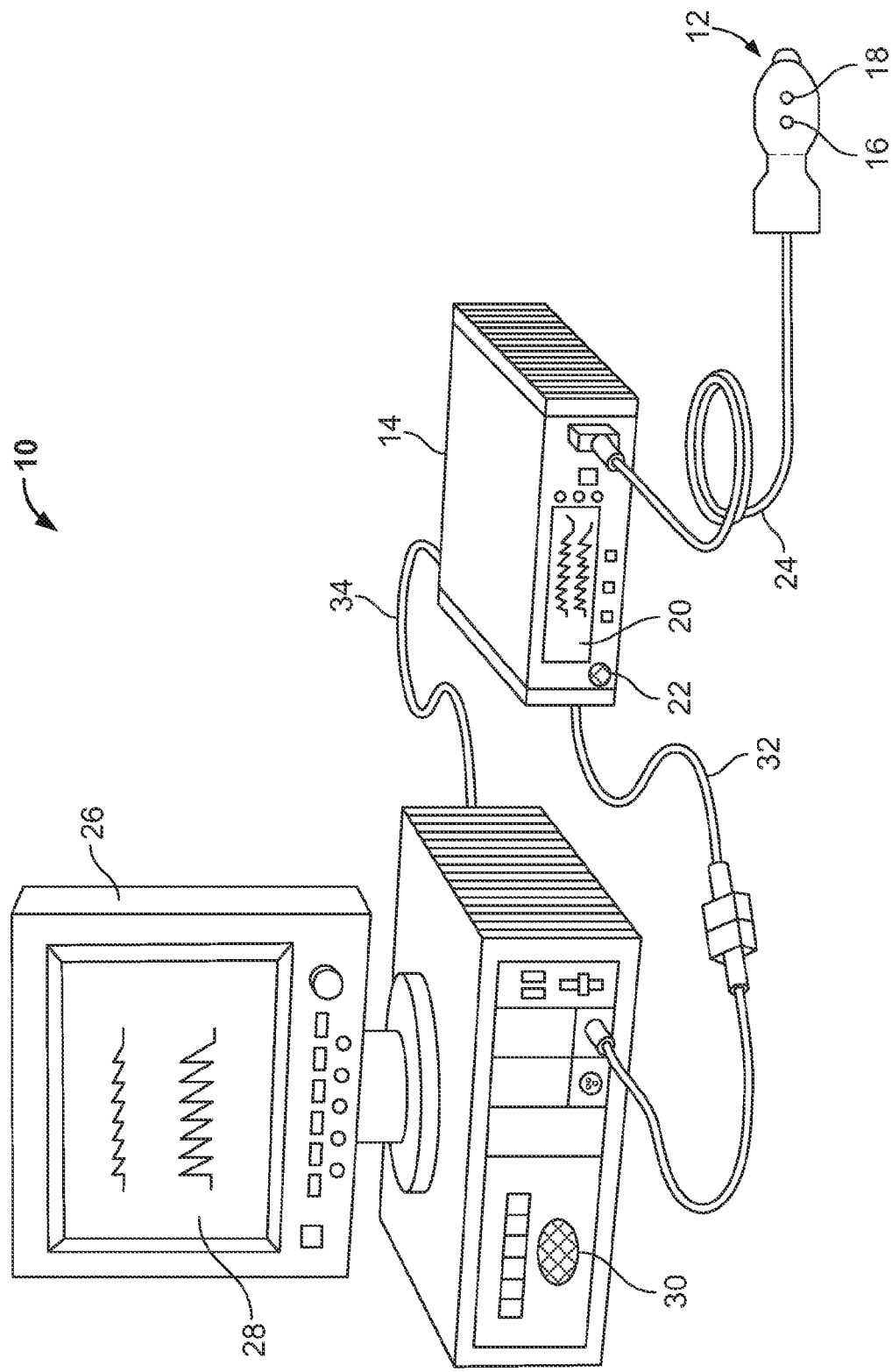
FIG. 1 shows an illustrative pulse oximetry system in accordance with some embodiments.

An oximeter is a medical device that is commonly used to determine the oxygen saturation of a patient's blood. One common type of oximeter is a pulse oximeter, which indirectly measures the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters are also used to measure the pulse rate of the patient. Pulse oximeters typically measure and display various blood flow characteristics including, but not limited to, the oxygen saturation of hemoglobin in arterial blood.

An oximeter is typically used with a light sensor that is placed at a site on a patient, typically a fingertip, toe, forehead or earlobe, or in the case of a neonate, across a foot. The oximeter passes light using a light source through blood perfused tissue and photoelectrically senses the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the PPG signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t) = I_o(\lambda)\exp(-(s\beta_o(\lambda)+(1-s)\beta_r(\lambda))Cl(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
Cl(t)=a combination of hemoglobin concentration and path length from emitter to detector as a function of time.

The traditional approach measures light absorption at two wavelengths (e.g., red and IR), and then calculates arterial blood oxygen saturation by solving for a "ratio of ratios" as follows:

1. First, the natural logarithm of (1) is taken ("log" will be used to represent the natural logarithm) for IR and red wavelengths $$\log I = \log I_o - (s\beta_o + (1-s)\beta_r)Cl(t) \quad (2)$$

2. (2) is then differentiated with respect to time $$\frac{d\log I}{dt} = -(s\beta_o + (1-s)\beta_r)\frac{dCl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R)+(1-s)\beta_r(\lambda_R)}{s\beta_o(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR})-\beta_r(\lambda_{IR})) - \frac{d\log I(\lambda_{IR})}{dt}(\beta_o(\lambda_R)-\beta_r(\lambda_R))}$$

Note in discrete time $$\frac{d \log I(\lambda, t)}{dt} \simeq \log I(\lambda, t_2) - \log I(\lambda, t_1)$$

Using log A-log B=log A/B, $$\frac{d \log I(\lambda, t)}{dt} \simeq \log\left(\frac{I(t_2, \lambda)}{I(t_1, \lambda)}\right)$$

So, (4) can be rewritten as $$\frac{\frac{d \log I(\lambda_R)}{dt}}{\frac{d \log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios," Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d \log I}{dt} = \frac{dI/dt}{I} \quad (6)$$

now (5) becomes $$\frac{\frac{d \log I(\lambda_R)}{dt}}{\frac{d \log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2, \lambda_{IR}) - I(t_1, \lambda_{IR})]I(t_1, \lambda_R)$$

$$y(t) = [I(t_2, \lambda_R) - I(t_1, \lambda_R)]I(t_1, \lambda_{IR})$$

$$y(t) = Rx(t) \quad (8)$$

FIG. 1 is an illustrative perspective view of a pulse oximetry system 10 in accordance with some embodiments. System 10 includes a sensor 12 and a pulse oximetry monitor 14. Sensor 12 includes an emitter 16 for emitting light at two or more wavelengths into a patient's tissue. A detector 18 is also provided in sensor 12 for detecting the light originally from emitter 16 that emanates from the patient's tissue after passing through the tissue.

Figure 2:
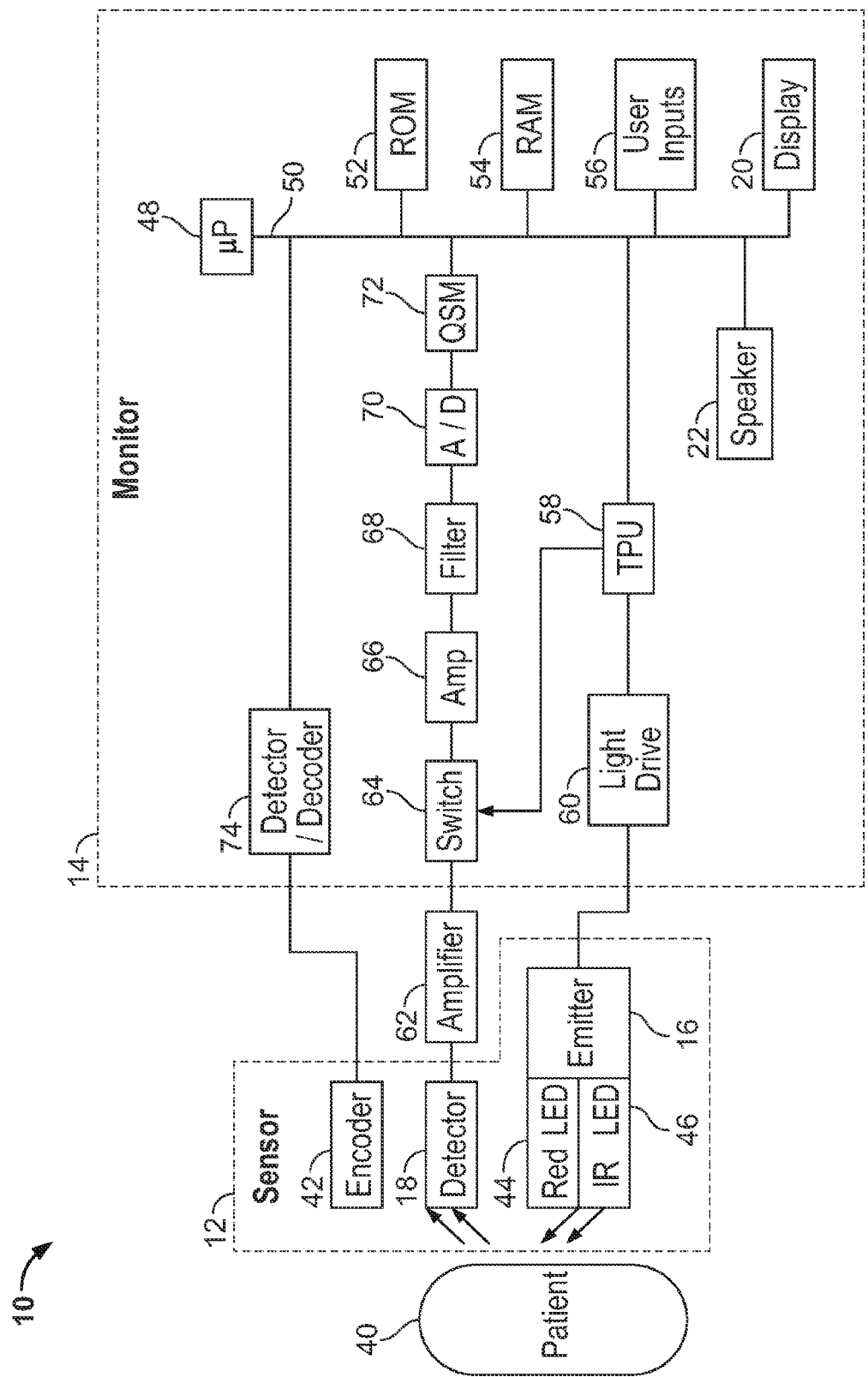
FIG. 2 is a block diagram of the illustrative pulse oximetry system of FIG. 1 coupled to a patient in accordance with some embodiments.

In some embodiments and as will be further described in relation to FIG. 2, system 10 includes a plurality of sensors forming a sensor array in lieu of single sensor 12. Each of the sensors of the sensor array may be a complementary metal oxide semiconductor (CMOS) sensor, photodiode, phototransistor, or charged coupled device (CCD) sensor, individually or in various combinations. In some embodiments, the sensor array is made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

In some embodiments, emitter 16 and detector 18 are on opposite sides of a digit such as a finger or toe, in which case the light that is emanating from the tissue has passed completely through the digit. In some embodiments, emitter 16 and detector 18 are arranged so that light from emitter 16 penetrates the tissue and is reflected by the tissue into detector 18, such as a sensor designed to obtain pulse oximetry data from a patient's forehead.

In some embodiments, the sensor or sensor array is connected to and draws its power from monitor 14 as shown. In some embodiments, the sensor is wirelessly connected to monitor 14 and includes its own battery or similar power supply (not shown). Monitor 14 may be configured to calculate physiological parameters based at least in part on data received from sensor 12 relating to light emission and detection. In some embodiments, the calculations are performed on the monitoring device itself and the result of the oximetry reading is passed to monitor 14. Further, monitor 14 may include a display 20 configured to display the physiological parameters or other information about the system. In some embodiments, monitor 14 also includes a speaker 22 to provide an audible sound that may be used in various other embodiments, such as for example, sounding an audible alarm in the event that a patient's physiological parameters are not within a predefined normal range.

In some embodiments, sensor 12, or the sensor array, is communicatively coupled to monitor 14 via a cable 24. In some embodiments, a wireless transmission device (not shown) or the like is used instead of or in addition to cable 24.

In some embodiments, pulse oximetry system 10 also includes a multi-parameter patient monitor 26. The monitor may be a cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery not shown) or by a conventional power source such as a wall outlet.

FIG. 2 is a block diagram of a pulse oximetry system, such as pulse oximetry system 10 of FIG. 1, which is coupled to a patient 40 in accordance with some embodiments. As used herein, a patient may be a subject or any other entity from which physiological signals are obtained. Certain illustrative components of sensor 12 and monitor 14 are illustrated in FIG. 2. Sensor 12 includes emitter 16, detector 18, and encoder 42. In some embodiments, emitter 16 is configured to emit at least two wavelengths of light (e.g., red and IR) into a patient's tissue 40. Hence, emitter 16 may include a red light emitting light source such as red light emitting diode (LED) 44 and an IR light emitting light source such as IR LED 46 for emitting light into the patient's tissue 40 at the wavelengths used to calculate the patient's physiological parameters. In some embodiments, the red wavelength is between about 600 nm and about 700 nm, and the IR wavelength is between about 800 nm and about 1000 nm. In certain implementations where a sensor array is used in place of single sensor, each sensor may be configured to emit a single wavelength. For example, a first sensor emits only a red light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In some embodiments, detector 18 is configured to detect the intensity of light at the red and IR wavelengths. Alternatively, each sensor in the array may be configured to detect an intensity of a single wavelength. In operation, light enters detector 18 after passing through the patient's tissue 40. Detector 18 converts the intensity of the received light into an electrical signal. The light intensity is directly related to the absorbance and/or reflectance of light in the patient's tissue 40. That is, when more light at a certain wavelength is absorbed or reflected, less light of that wavelength is received from the tissue by the detector 18. After converting the received light to an electrical signal, detector 18 sends the signal to monitor 14, where physiological parameters are calculated based on the absorption of the red and IR wavelengths in the patient's tissue 40.

In some embodiments, encoder 42 contains information about sensor 12, such as what type of sensor it is (e.g., whether the sensor is intended for placement on a forehead or digit) and the wavelengths of light emitted by emitter 16. This information may be used by monitor 14 to select appropriate algorithms, look-up tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 includes a memory on which one or more of the following information may be stored for communication to monitor 14: the type of the sensor 12, the wavelengths of light emitted by emitter 16, the particular wavelength each sensor in the sensor array is monitoring, a signal threshold for each sensor in the sensor array, any other suitable information, or any combination thereof.

In some embodiments, signals from detector 18 and encoder 42 are transmitted to monitor 14. In some embodiments, monitor 14 includes a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In some embodiments, a time processing unit (TPU) 58 provides timing control signals to a light drive circuitry 60, which controls when emitter 16 is illuminated and multiplexed timing for the red LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In some embodiments, there are multiple separate parallel paths having amplifier 66, filter 68, and A/D converter 70 for multiple light wavelengths or spectra received.

In some embodiments, microprocessor 48 determines the patient's physiological parameters, such as $SpO_2$ and pulse rate, using various algorithms and/or look-up tables based on the value of the received signals and/or data corresponding to the light received by detector 18. In some embodiments, microprocessor 48 is used for signal processing. For example, microprocessor 48 may calculate an archetype transform using a weighted averaging scheme. Signals corresponding to information about patient 40, and particularly about the intensity of light emanating from a patient's tissue over time, are transmitted from encoder 42 to a decoder 74. These signals may include, for example, encoded information relating to patient characteristics. Decoder 74 translates these signals to enable the microprocessor to determine the thresholds based on algorithms or look-up tables stored in ROM 52. User inputs 56 may be used to enter information about the patient, such as age, weight, height, diagnosis, medications, treatments, and so forth. In some embodiments, display 20 exhibits a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations, such as filtering, that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

Figure 3:
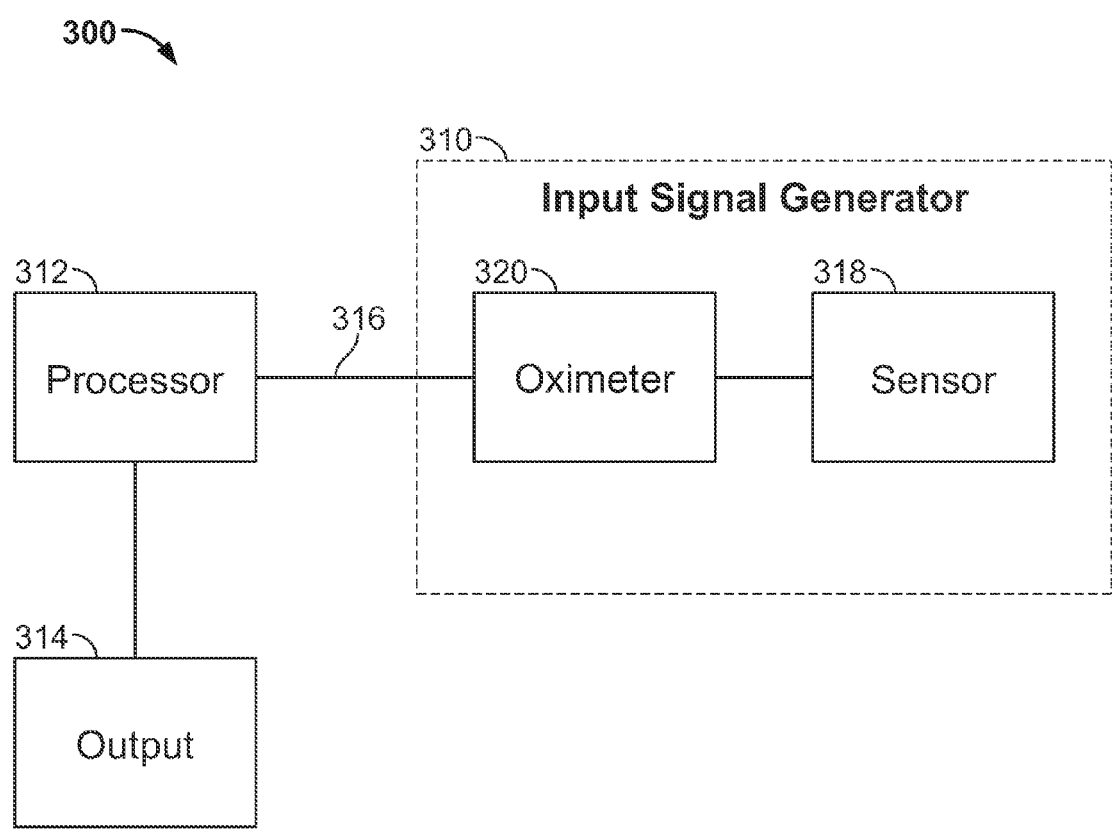
FIG. 3 is a block diagram of an illustrative signal processing system in accordance with some embodiments.

FIG. 3 is a block diagram of an illustrative signal processing system in accordance with some embodiments. In some embodiments, input signal generator 310 generates an input signal 316. As illustrated, input signal generator 310 includes oximeter 320 coupled to sensor 318, which provides as input signal 316, a PPG signal. It will be understood that input signal generator 310 may include any suitable signal source, signal generating data, signal generating equipment, or any combination thereof to produce signal 316. Signal 316 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In some embodiments, signal 316 is coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform any suitable signal processing of signal 316 to filter signal 316, such as any suitable band-pass filtering, adaptive filtering, closed-loop filtering, and/or any other suitable filtering, and/or any combination thereof.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 312 to, for example, store threshold values and/or look-up table values, as discussed further in relation to FIGS. 6 and 9.

Processor 312 is coupled to output 314. Output 314 may be any suitable output device such as, for example, one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 is implemented as part of sensor 12 and monitor 14, and the processor 312 is implemented as part of monitor 14.

FIG. 4(*a*) shows an illustrative PPG signal 402 obtained by a pulse oximeter in accordance with some embodiments. Sensor 318 (FIG. 3) provides PPG signal 402 shown in FIG. 4(*a*) as an input to processor 312 (FIG. 3). PPG signal 402 may correspond to a PPG signal associated with a red wavelength or an IR wavelength.

PPG signal 402 includes two signal components as shown in FIG. 4(*a*). PPG signal 402 includes a pulsatile component 406 and a baseline modulation component 404. Pulsatile component 406 may be attributed to variations in the subject's blood flow that are caused by cardiac activity. Baseline modulation component 404 is attributed to other variations in the subject's blood flow that are caused by the subject's respiration activity. In some instances, the subject's respiration activity is influenced by or is due to the subject using a ventilator. Baseline modulation component 404 may be indicative of the subject's venous blood flow.

FIG. 4(*b*) shows a schematic 404 of the PPG signal of FIG. 4(*a*) that has been filtered at or around a respiration rate (e.g., 0.25 Hz) to remove the pulsatile component 406 and preserve the baseline modulation component 404. Baseline modulation component 404 shows an illustration of the signal obtained after filtering PPG signal 402 to remove pulsatile component 406. Filtering techniques for obtaining baseline modulation component 404 from PPG signal 402 are described in detail with respect to the steps of FIG. 6 below. Baseline modulation component 404 includes certain characteristics. For example, extremum 408, which corresponds to a maximum of the baseline modulation component 404, may be a feature used to characterize the baseline modulation component 404. Use of such characteristics is explained further with respect to FIGS. 5(*a*) and 5(*b*) below.

Figure 5A:
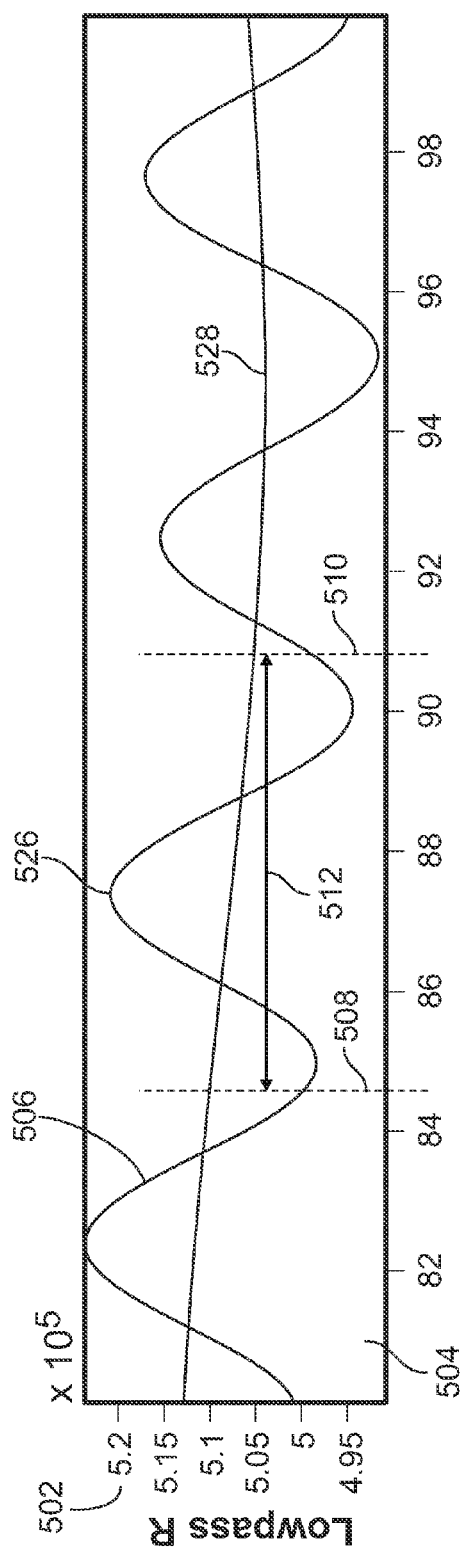
FIGS. 5(a) and 5(b) show illustrative schematics of a filtered red PPG signal and a filtered infrared PPG signal, respectively, in accordance with some embodiments.
Figure 5B:
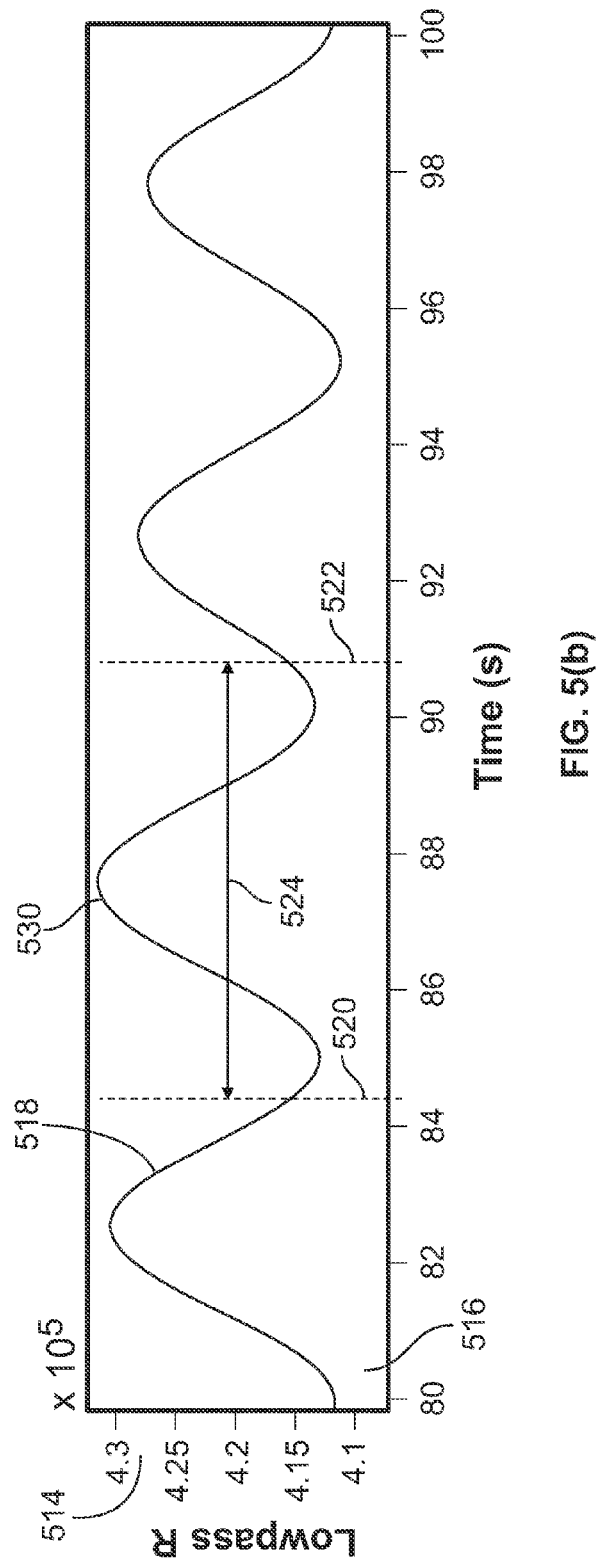

FIGS. 5(*a*) and 5(*b*) show illustrative schematics of a filtered red PPG signal 506 and a filtered infrared PPG signal 518, respectively, in accordance with some embodiments. The PPG signals may be taken from a pulse oximeter probe placed, for example, on a subject's chest wall. Filtered red PPG signal 506 is obtained by low-pass filtering a red PPG signal to extract respiratory modulations. Y-axis 502 of FIG. 5(*a*) denotes the amplitude of the respiratory modulations from the red PPG signal 506. X-axis 504 of FIG. 5(*a*) denotes time, in seconds, increasing from left to right. The line 528 represents the mean value over time (i.e., baseline) of the respiratory modulations. The baseline 528 can be computed, for example, by low-pass filtering the respiratory modulations at a frequency lower than the respiration rate.

In some embodiments, time points 508 and 510 denote the beginning and the end points of a time window 512 within which an extremum 526 is identified. The duration of time window 512 is the difference between time points 510 and 508. In some embodiments, time window 512 has duration of 6 seconds. Time windows of longer or shorter time durations than 6 seconds may also be used depending on the context or the subject's condition.

FIG. 5(*b*) shows a filtered infrared PPG signal 518 in accordance with some embodiments. Filtered red PPG signal 518 is obtained by low-pass filtering an infrared PPG signal to extract the baseline modulation component. Y-axis 514 of FIG. 5(*b*) denotes the amplitude of filtered infrared PPG signal 518. X-axis 516 of FIG. 5(*b*) denotes time, in seconds, increasing from left to right. In some embodiments, time points 520 and 522 denote the beginning and the end points of a time window 524 within which an extremum 530 may be identified. The duration of time window 524 is the difference between time points 520 and 522. In some embodiments, time window 524 has a duration of 6 seconds. Time windows of longer or shorter time durations than 6 seconds may also be used depending on the context or the subject's condition.

Depending on which physiological condition of the subject is being determined, either the pulsatile component 406 or the baseline modulation component 404, or both components, may be utilized. For example, in some embodiments, pulsatile component 406 is utilized for determining the subject's arterial oxygen saturation. In some embodiments, sites on a subject's body conventionally used for oximetry (e.g., finger, forehead or ear) are used to obtain the red and the infrared PPG signals used for determining the subject's arterial oxygen saturation.

Respiration Modulation

Figure 6:
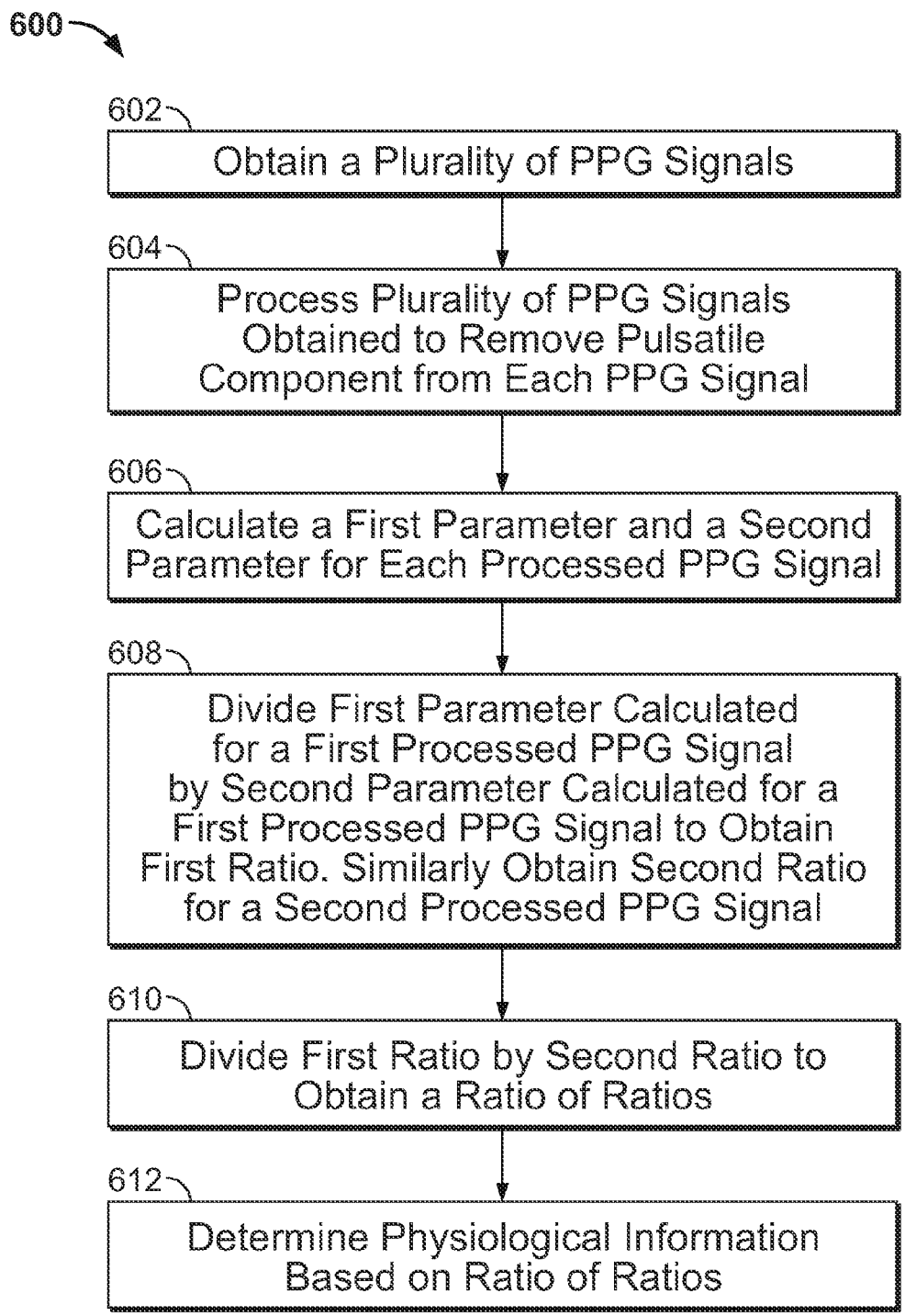
FIG. 6 is a flow chart of illustrative steps 600 for determining a ratio of ratios based on respiration modulation signals in accordance with some embodiments.

The baseline modulation component 404 may be utilized for determining the subject's venous oxygen saturation, as discussed in relation to FIG. 6. In some embodiments, because determining the subject's venous oxygen saturation does not require a cardiac pulsatile component, alternative sites on a subject's body not conventionally used for oximetry are used to obtain the red and the infrared PPG signals. For example, optical or other suitable techniques may be used to obtain the red and the infrared PPG signals from deeper regions in a subject's body for use in determining the subject's venous oxygen saturation. Such techniques provide information from deeper or more central parts of the subject's body and may permit more accurate determinations of the subject's venous oxygen saturation.

In some embodiments, the arterial oxygen saturation and the venous oxygen saturation, determined using pulsatile component 406 and baseline modulation component 404, respectively, are used for determining the subject's cardiac output. The use of the saturation values for determining cardiac output is described with respect to FIGS. 17-19.

Determination of venous oxygen saturation is discussed with respect to FIG. 6. FIG. 6 illustrates how to obtain a signal (step 602) and then how to process the signal to obtain a venous oxygen saturation value (steps 604, 606, 608, 610, and 612). The steps of flow chart 600 may be performed by processing equipment such as processor 316 of FIG. 3, microprocessor 48 of FIG. 2, or any suitable processing device. The steps of flow chart 600 may be performed by a digital processing device, or implemented in analog hardware. It will be noted that the steps of flow chart 600 may be performed in any suitable order, and one or more steps may be omitted entirely according to the context and application.

At step 602, a plurality of signals is obtained. A signal (e.g., a PPG signal) may be obtained from any suitable source (e.g., sensor 12 of FIG. 2) using any suitable technique. A sensor from which a signal is obtained may include any of the physiological sensors described herein, or any other sensor. An obtained signal may be signal 402 as shown in FIG. 4(*a*). An obtained signal may include multiple signals, for example, in the form of a multi-dimensional vector signal or a frequency-multiplexed or time-multiplexed signal. In some embodiments, the plurality of signals obtained at step 602 include two or more PPG signals, which may be measured at two or more respective body sites of a subject.

The plurality of signals obtained at step 602 include first and second physiological signals. In some embodiments, a first signal is a PPG signal corresponding to a red wavelength, and a second signal is a PPG signal corresponding to an infrared wavelength. The red and infrared wavelengths may correspond to those used in traditional pulse oximetry, or entirely different wavelengths may be used. In some embodiments, each of the first and second signals obtained at step 602 includes a cardiac pulsatile component and a baseline modulation component, such as pulsatile component 406 of FIG. 4(*a*) and baseline modulation component 404 of FIG. 4(*b*). In some embodiments, first and second signals are obtained by first and second sensors located at approximately the same body site of a subject. In some embodiments, first and second signals are obtained by first and second sensors located at different body sites of a subject. For example, first and second signals included in a plurality of signals may be electronic signals from pulse oximetry sensors located at two different body sites of a subject. It will be noted that the steps of flow diagram 600 may be applied to any number of obtained signals in accordance with the techniques described herein.

At step 604, one or more of the plurality of signals obtained at step 602 is processed to remove pulsatile components such as pulsatile component 406 and generate a corresponding respiratory modulation signal. The processing may occur when the signal is acquired in step 602 or as a subsequent processing step. A processing operation may be performed by any suitable processing device, such as processor 312 (FIG. 3), which may be a general-purpose computing device or a specialized processor. A processing operation may be performed by a separate, dedicated device, or by a series of devices (e.g., an analog filter and a programmed microprocessor). Any of the processing steps described herein may be used to remove the pulsatile component from the plurality of signals obtained at step 602.

A processing operation may transform the original and/or transformed signals into any suitable domain. In some embodiments, the processing at step 604 includes transforming a signal into another domain, for example, a Fourier, wavelet, spectral, scale, time, time-spectral, or time-scale domain, or any transform space. Wavelet transforms are further discussed below with respect to FIGS. 12(a)-(f).

The processing at step 604 may include filtering a signal or mathematically manipulating one or multiple signals. For example, a processed signal may be based at least in part on past values of a signal, such as signal 316 (FIG. 3), which may be retrieved by processor 312 (FIG. 3) from a memory such as a buffer memory or RAM 54 (FIG. 2). Many examples of processing operations are discussed in detail herein, but it will be understood that the techniques of the present disclosure are not limited to these examples.

The processing operations of step 604 may include any one or more of the following: compressing, multiplexing, modulating, up-sampling, down-sampling, smoothing, taking a median or other statistic of the obtained signal, removing erroneous regions of the obtained signal, or any combination thereof. In some embodiments, a normalization step is performed which divides the magnitude of a signal obtained at step 602 by a value. This value may be based on at least one of the maximum of the obtained signal, the minimum of the obtained signal and the mean of the obtained signal. In some embodiments, a signal obtained at step 602 is normalized by dividing the signal by a DC component. In some embodiments, a signal obtained at step 602 is normalized by dividing the signal by the standard deviation of the signal computed over a time window. In some embodiments, the processing operations at step 604 include one or more mathematical manipulations. Mathematical manipulations may include any linear or non-linear combination or signals or portions of signals, and may be performed in any suitable domain (e.g., time, frequency and wavelet domains).

In some embodiments, the processing operations at step 604 include one or more time derivatives. A time derivative may be calculated by processor 312 (FIG. 3). A time derivative may be calculated by any of a number of derivative/gradient determination and approximation techniques, including those suitable for sampled data (e.g., forward difference, backward difference, central difference, higher-order methods, and any automated numerical or symbolic differentiation method).

In some embodiments, the processing operations at step 604 include filtering using any suitable filtering technique. For example, a signal received at sensor unit 12 (FIGS. 1 and 2) may be filtered at step 604 by low pass filter 68 (FIG. 2) prior to undergoing additional processing at microprocessor 48 (FIG. 2) within patient monitoring system 10 (FIGS. 1 and 2). Low-pass filter 68 (FIG. 2) may selectively remove frequencies that may later be ignored by further processing or analysis steps, which may advantageously reduce computational time and memory requirements. In some embodiments, one or more signals obtained at step 602 are low- or band-pass filtered at step 604 to remove high frequencies. In some embodiments, one or inure signals obtained at step 602 are filtered at step 604 to remove a DC component. In some embodiments, an obtained PPG signal is low-pass filtered at step 604 to pass frequencies in the approximate range 0-0.25 Hz to remove non-respiratory frequencies. In some embodiments, an obtained PPG signal is band-pass filtered at step 604 to pass selected frequencies. In some embodiments, the cutoff frequencies of such a filter are selected based on the measured heart rate or respiratory rate of the subject under test. In some embodiments, the cutoff frequencies of a filter are chosen based on the frequency response of the hardware platform underlying patient monitoring system 10 (FIGS. 1 and 2). In some embodiments, a windowing operation is performed at step 604 to suppress or amplify one or more portions of a signal obtained at step 602.

Different processing operations may be applied to any one or both of the first and second signals obtained at step 602 and/or any components of a multi-component signal. For example, different operations may be applied to a signal taken from a first body site and a signal taken from a second body site.

Any of the operations described herein may be applied to a portion or portions of an obtained signal. An operation may be broken into one or more stages performed by one or more devices within signal processing system 300 of FIG. 3 (which may itself be a part of patient monitoring system 10 of FIGS. 1 and 2). For example, a filtering technique may be applied by input signal generator 310 (FIG. 3) prior to passing the resulting input signal 316 (FIG. 3) to processor 312 (FIG. 3), where the input signal may undergo a transformation and/or the calculation of a time derivative. Embodiments of the steps of flow diagram 600 may include any of the operations described herein performed in any suitable order.

At step 606, a first parameter and a second parameter are calculated for each respiratory modulation signal generated in step 604. In some embodiments, the first and second parameters correspond to an amplitude and a mean baseline of a respiratory modulation signal. In some embodiments, a first parameter is calculated at step 606 based on features of the respiratory modulation signal. A feature of a signal may be any characterization of that signal, including for example, the temporal location of an extremum (e.g., maxima or minima), the spatial location of an extremum, or the amplitude of an extremum. In some embodiments, a feature of a processed signal is a calculated quantity based at least in part on a portion of the processed signal. For example, a feature of a processed signal may be an average or weighted average of the processed signal over a window, a baseline value over a window, a magnitude or phase of a frequency component of a Fourier transform, a magnitude or phase or scale of a continuous wavelet transform, or any suitable calculated feature.

In some embodiments, only a portion or portions of a respiratory modulation signal are analyzed to identify features of interest. For example, certain segments of a signal may be identified, and only those segments may be analyzed for the presence of certain features (e.g., extrema). Identifying segments of a signal may occur before or after any one or more of the processing operations and thus the segments may be identified prior to completing the processing operations. Focusing the calculation of the first parameter on identified segments of the respiratory modulation signals may improve the efficiency of carrying out the steps of flow diagram 600 by reducing the time spent analyzing portions of the signals that are less relevant to the information of interest (e.g., the noisier regions).

Figure 4A:
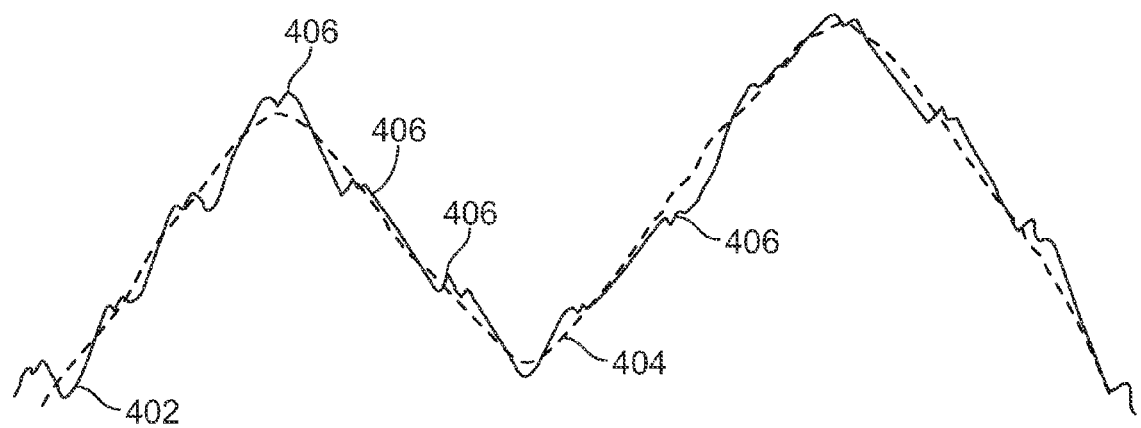
FIG. 4(a) shows an illustrative PPG signal in accordance with some embodiments.
Figure 4B:
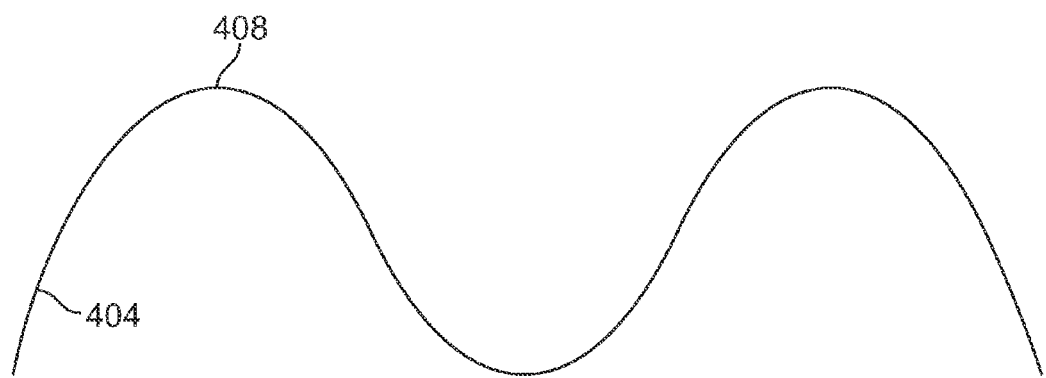
FIG. 4(b) shows an illustrative filtered PPG signal in accordance with some embodiments.
Figure 4C:
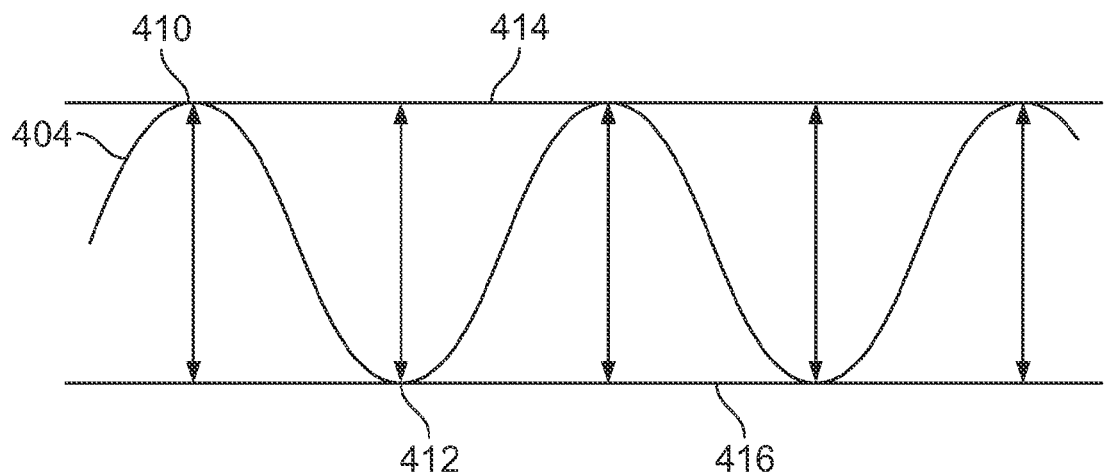
FIG. 4(c) shows an illustrative respiratory modulation signal in accordance with some embodiments.
Figure 4D:
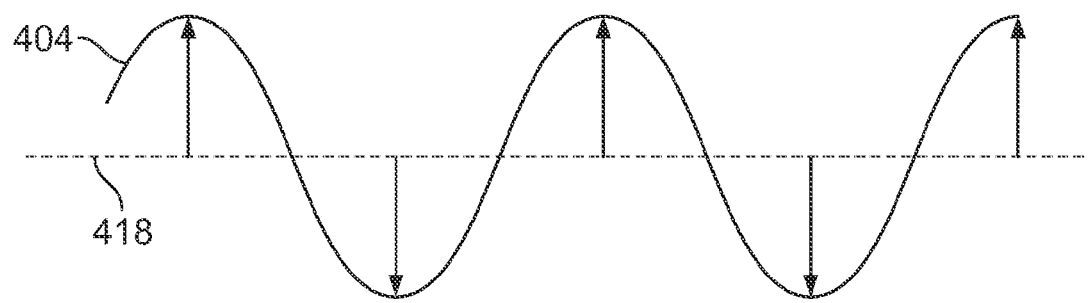
FIG. 4(d) shows an illustrative respiratory modulation signal in accordance with some embodiments.

In some embodiments, calculating a first parameter includes identifying an amplitude of a respiratory modulation signal. For example, as shown in FIG. 4(c), the maxima 410 and minima 412 of respiratory modulation signal 404 can be identified and lines 414 and 416 may be fitted to the successive maxima and minima, forming an envelope around the signal. The amplitude may be defined as the height of the envelope (i.e., the distance between lines 414 and 416). Alternatively, as shown in FIG. 4(d), a baseline signal 418 of respiratory modulation signal 404 can be defined. The baseline signal 418 may be computed by low-pass filtering the respiratory modulation signal at a frequency below that of the respiration rate (e.g., 0.1 Hz) or by any other suitable method. The distance from respiratory modulation signal 404 and the baseline signal 418 may be computed and averaged over a number of cycles of the respiratory modulation signal. Other suitable methods for computing an amplitude of respiratory modulation signal may also be employed.

Continuing with step 606, a second parameter is also calculated for each of the respiratory modulation signals. This order of processing and calculations is merely illustrative; it will be understood that either of the processing steps and the first and second parameter calculating steps may be performed in any suitable order or simultaneously.

In some embodiments, the second parameter calculated at step 606 includes one or more summary statistics of a respiratory modulation signal. The second parameter may be calculated for each of the respiratory modulation signals. In one embodiment, the second parameter is the mean baseline value of the respiratory modulation signal. The baseline may be computed as discussed above in connection with the calculation of the first parameter and then averaged over a suitable time window to form a mean baseline value. In another embodiment, the second parameter may be a value associated with the mean amplitude of a respiratory modulation signal. In some embodiments, the number of amplitudes used to calculate the mean amplitude is predetermined. In some embodiments, the number of amplitudes used to calculate the mean amplitude is variable. In some embodiments, the mean amplitude is calculated over a time window.

At step 608, a ratio is computed for each respiratory modulation signal. The ratio may be the quotient of the first and second parameters computed from that signal. In some embodiments, the ratio is the quotient of the amplitude of the respiratory modulation signal and the mean baseline value of the respiratory modulation signal. In some embodiments a first respiratory modulation signal is based on a PPG signal corresponding to a red wavelength and a second respiratory modulation signal is based on a PPG signal corresponding to an infrared wavelength. In some embodiments, logarithms of the first and second ratios are calculated and stored in ROM 52 or RAM 54 (FIG. 1). Any other suitable mathematical function may also be used.

At step 610, a ratio of ratios is calculated, which may be used to determine a venous oxygen saturation value, as discussed in relation to step 612. In some embodiments, the ratio of ratios is calculated by dividing the logarithm of the first ratio obtained for the red PPG signal by the logarithm of the second ratio obtained for the infrared PPG signal. That is, a ratio of ratios, RoR, is calculated using the equation $$RoR = \frac{\ln(R_A/R_B)}{\ln(IR_A/IR_B)}, \quad (9)$$

where ln represents the logarithm operator, $R_A$ is the amplitude of the baseline modulation component of a red PPG signal, $R_B$ is the mean baseline value of the baseline modulation component of a red PPG signal, $R_A/R_B$ represents the first ratio corresponding to a red PPG signal, $IR_A$ is the amplitude of the baseline modulation component of an infrared PPG signal, $IR_B$ is the mean baseline value of the baseline modulation component of an infrared PPG signal, and $IR_A/IR_B$ represents the second ratio corresponding to an infrared PPG signal. The calculation of the ratio of ratios may be performed by processor 312 (FIG. 3) and the resulting numerical value may be stored in ROM 52 or RAM 54 (FIG. 1). In some embodiments, the ratio of ratios is calculated without taking a logarithm of the first ratio corresponding to a red PPG signal or the second ratio corresponding to an infrared PPG signal. In yet other embodiments, RoR can be computed alternatively as a ratio of AC/DC signals or a ratio of the derivatives, as described in equation (7); or the values of $R_A$, $R_B$, $IR_A$, $IR_B$ in equation (9) can be taken from points in time corresponding to local maxima and minima or other signal points along baseline modulation.

At step 612, information about the subject based at least in part on the ratio of ratios is determined. In some embodiments, information determined at step 612 is physiological information. For example, physiological information determined at step 612 may include venous oxygen saturation.

In some embodiments, the ratio of ratios calculated at step 610 is used to determine the subject's venous oxygen saturation by using a look-up table. The look-up table may include entries associating a numerical value of the ratio of ratios to a value of venous oxygen saturation. For example, a ratio of ratios value of about 1.1 may correspond to a venous oxygen saturation value of about 80%; or when sensor 18 (FIG. 1) is placed at the subject's finger, the ratio of ratios value may fall in the range 0.5-0.7 which may correspond to a venous oxygen saturation value in the range 90-99%; or when sensor 18 (FIG. 1) is placed at the subject's chest wall, the ratio of ratios value may fall in the range 0.4-1.3 which may correspond to a venous oxygen saturation value in the range 70-100%. In some embodiments, the entries of the look-up table are predetermined or are determined based on calibrating test ratio of ratios values to sample venous oxygen saturation values. In some embodiments, the entries of the look-up table account for the ambient temperature by calibrating the venous oxygen saturation values appropriately. For example, a given ratio of ratios value that corresponds to a given venous oxygen saturation value at a given temperature may correspond to a venous oxygen saturation value higher or lower than the given venous oxygen saturation value depending on whether the temperature is higher or lower than the given temperature. The look-up table may be stored in ROM 52 or RAM 54 (FIG. 1) or may be stored in external storage (not shown). In some embodiments, the look-up table is a Server Query Language (SQL) or any other appropriate database. Alternatively, the subject's venous oxygen saturation can be computed from the ratio of ratio values according to a numerical equation following the format of the equation shown immediately below equation (5) or other suitable function that can be used to describe the curve corresponding to the relationship between the ratio of ratios and venous oxygen saturation.

In some embodiments, the subject's arterial oxygen saturation is determined in a manner similar to the process described in flow chart 600. For example, at step 606 a pulsatile component of each of the plurality of signals may be identified based on the processing techniques described above. Steps 608-612 may then be performed on the pulsatile components, identified respectively for the red PPG signal and the infrared PPG signal, for determining the subject's arterial oxygen saturation.

In some embodiments, the subject's arterial oxygen saturation and venous oxygen saturation are determined in parallel by processing equipment. Parallel determination of the subject's arterial oxygen saturation and venous oxygen saturation allows the monitoring of a differential desaturation characteristic between the subject's arterial oxygen saturation and venous oxygen saturation. Monitoring and comparing the differential desaturation advantageously allows for a more robust indication of a subject's oxygen saturation. In some embodiments, the subject's arterial oxygen saturation is determined using red and infrared PPG signals obtained from a sensor placed at a first site on the subject and the subject's venous oxygen saturation is determined using red and infrared PPG signals obtained from a sensor placed at a second site on the subject.

After information about the subject is determined at step 612, the information determined may be output to an output device through a graphical representation, quantitative representation, qualitative representation, or combination of representations via output 314 (FIG. 3) and may be controlled by processor 312 (FIG. 3). In some embodiments, output 314 (FIG. 3) transmits physiological information by any means and through any format useful for informing a patient, a care provider, or a third party, of a patient's status and records the physiological information to a storage medium. Quantitative and/or qualitative information provided by output 314 (FIG. 3) may be displayed on a display (e.g., display 28 of FIG. 1). A graphical representation may be displayed in one, two, or more dimensions and may be fixed or change with time. A graphical representation may be further enhanced by changes in color, pattern, or any other visual representation. Output 314 (FIG. 3) may communicate the information by performing at least one of the following: presenting a screen on a display; presenting a message on a display; producing a tone or sound; changing a color of a display or a light source; producing a vibration; and sending an electronic message. Output 314 (FIG. 3) may perform any of these actions in a device close to a patient, or at a mobile or remote monitoring device as described previously. In some embodiments, output 314 (FIG. 3) produces a continuous tone or beeping whose frequency changes in response to changes in a process of interest, such as a physiological process. In some embodiments, output 314 (FIG. 3) produces a colored or flashing light that changes in response to changes in a physiological process of interest.

After or during the information determination of step 612, the steps of flow diagram 600 may be repeated. New signals may be obtained, or the information determination may continue on another portion of one or more of the previously obtained signal(s). In some embodiments, processor 312 (FIG. 3) continuously or periodically performs steps 602-612 and updates the information (e.g., as the patient's condition changes). The process may repeat indefinitely, until there is a command to stop the monitoring and/or until some detected event occurs that is designated to halt the monitoring process. For example, it may be desirable to halt a monitoring process when a detected noise has become too great, a measurement quality has become too low, or, in a patient monitoring setting, when a patient has undergone a change in condition that can no longer be sufficiently well-monitored in a current monitoring configuration. In some embodiments, processor 312 (FIG. 3) performs the steps of flow diagram 600 at a prompt from a care provider via user inputs 56 (FIG. 2). In some embodiments, processor 312 (FIG. 3) performs the steps of flow diagram 600 at intervals that change according to patient status. For example, the steps of flow diagram 600 may be performed more often when a patient is undergoing rapid changes in physiological condition, and performed less often as the patient's condition stabilizes.

The steps of flow diagram 600 may be executed over a sliding window of a signal. For example, the steps of flow diagram 600 may involve analyzing the previous samples of the signal, or the samples of the signal obtained in the previous units of time. The length of the sliding window over which the steps of flow diagram 600 is executed may be fixed or dynamic. In some embodiments, the length of the sliding window is based at least in part on the noise content of a signal. For example, the length of the sliding window may increase with decreasing measurement quality and/or increasing noise, as may be determined by a measurement quality assessment and/or a noise assessment. A subject's venous oxygen saturation may be monitored continuously using a moving PPG signal. PPG signal detection means may include a pulse oximeter and associated hardware, software, or both. A processor may continuously analyze the signal from the PPG signal detection means in order to continuously monitor a subject's venous oxygen saturation.

Any number of computational and/or optimization techniques may be performed in conjunction with the techniques described herein. For example, any known information regarding the physiological status of the patient may be stored in memory (e.g., ROM 52 or RAM 54 of FIG. 2). Such known information may be keyed to the characteristics of the patient, which may be input via user inputs 56 (FIG. 2) and used by monitor 14 (FIGS. 1 and 2) to, for example, query a look-up table and retrieve the appropriate information. Additionally, any of the calculations and computations described herein may be optimized for a particular hardware implementation, which may involve implementing any one or more of a pipelining protocol, a distributed algorithm, a memory management algorithm, or any suitable optimization technique.

The steps of flow chart 600 describe using the ratio of ratios to estimate a subject's venous oxygen saturation. The ratio of ratios may also be used to determine and evaluate the signal quality of the PPG signal itself, as discussed in relation to FIGS. 7(a)-11. For example, the ratio of ratios may be used to determine the likelihood that modulations in PPG signals are caused by respiration, as opposed to being an artifact of a patient's motion.

Figure 7C:
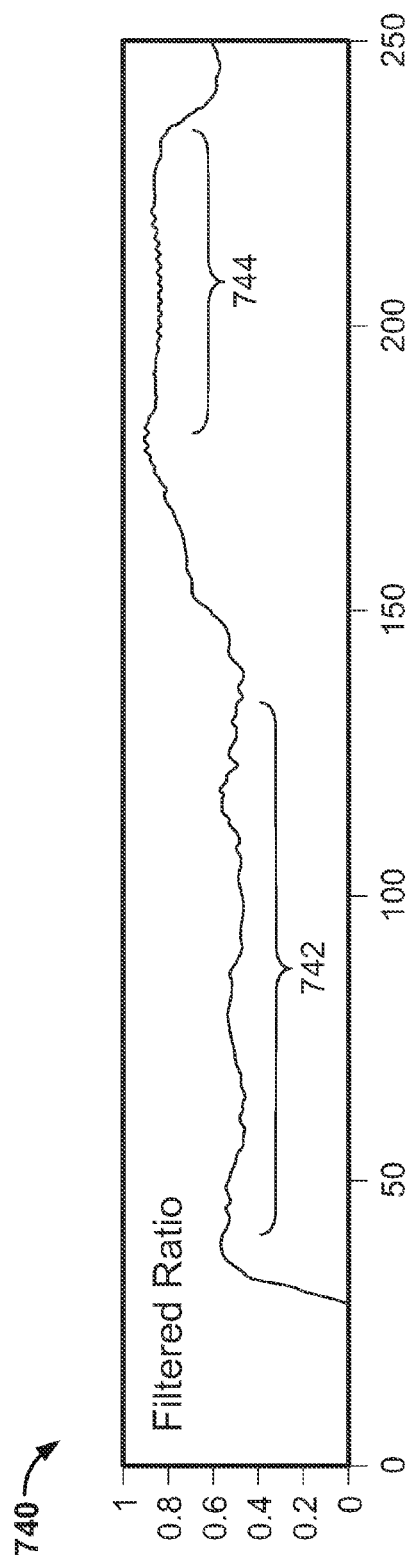
FIG. 7(c) shows an illustrative filtered ratio signal of the illustrative ratio signal of FIG. 7(b) in accordance with some embodiments.

FIG. 7(a) shows an illustrative plot 700 of normalized respiration modulation signals derived from red and infrared PPG signals in accordance with some embodiments. The PPG signals may be obtained from, for example, sensor 12 of FIGS. 1 and 2, or sensor 318 of FIG. 3. One or both of the PPG signals may be provided as part of input signal 316 (FIG. 3) from sensor 318. The PPG signals from which illustrative plot 700 is derived are obtained from a test time series of a subject's breathing. During the test, the subject breathed at 15 breaths per minute (4-second breaths). Different types of breathing resulted in sections of varying amplitudes in plot 700. At the beginning of the test, the subject breathed freely, without resistance, as indicated by section 702 of plot 700. In the next part of the test, the subject breathed through a resistive element for 60 seconds, as indicated by section 704 of plot 700. Examples of resistive elements include a small bore tube, a hand partially placed over the mouth, or a porous material placed over the mouth. Such resistive elements are typically placed in or over the mouth and the nose is closed off to force the subject to breathe only through the element. After the resistive breathing, the subject once again breathed freely, as indicated by section 712 of plot 700. Later in the test, the subject breathed while moving a hand from a high to low position in 4-second cycles. The effect of this motion on the PPG signals is seen in section 714 of plot 700.

The PPG signals obtained during the test time series may be low-pass filtered, illustratively at 0.5 Hz, in order to remove the cardiac pulse components but retain the respiration components. Baseline signals may be generated by low-pass filtering the PPG signals at another frequency, illustratively at 0.1 Hz. For each PPG signal, the baseline signal may be removed from the respiration component, and then the result may be divided by the baseline signal to give a normalized respiration modulation signal for each PPG signal, as shown in plot 700 of FIG. 7(a). The red PPG normalized respiration modulation signal 708 and the infrared PPG normalized respiration modulation signal 710 in FIG. 7(a) are more easily distinguished from one another in zoomed-in portion 706 of plot 700. In some embodiments, the normalized respiration modulation signals are processed according to the illustrative steps of flow chart 600 (FIG. 6).

FIG. 7(b) shows an illustrative ratio signal 720 obtained by dividing the red and infrared signals of FIG. 7(a) by each other in accordance with some embodiments. For example, the red PPG normalized respiration modulation signal 708 in FIG. 7(a) may be divided by the infrared PPG normalized respiration modulation signal 710 in FIG. 7(a). The division may be performed by processing equipment such as processor 316 of FIG. 3, microprocessor 48 of FIG. 2, or any suitable processing device. If the red PPG normalized respiration modulation signal 708 is divided by the infrared PPG normalized respiration modulation signal 710, discontinuities in ratio signal 720 may appear where infrared PPG normalized respiration modulation signal 710 goes through zero. If the infrared PPG normalized respiration modulation signal 710 is divided by the red PPG normalized respiration modulation signal 708, discontinuities in ratio signal 720 may appear where red PPG normalized respiration modulation signal 708 goes through zero.

FIG. 7(e) shows an illustrative filtered ratio signal 740 obtained by taking a median value of the illustrative ratio signal 720 of FIG. 7(b) over a 20-second window in accordance with some embodiments. Filtered ratio signal 740 exhibits distinctly different levels, indicated by sections 742 and 744, during the motion and no-motion portions of the test time series used to generate FIGS. 7(a)-(b). In some embodiments, filtered ratio signal 740 is used as an indication of modulations in one or more PPG signals being wholly or partly due to motion. For example, low values as in section 742 of filtered ratio signal 740 may correspond to modulations due to respiration. High values as in section 744 of filtered ratio signal 740 may correspond to modulations due wholly or partly to the subject's motion.

Figure 8:
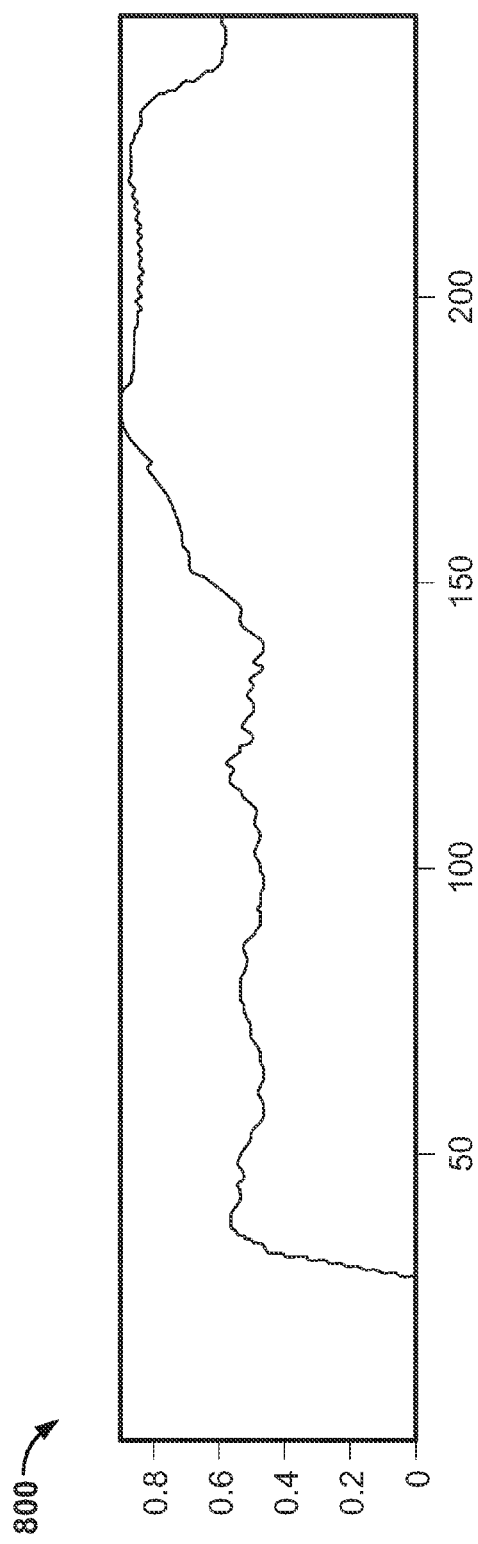
FIG. 8 shows an illustrative mean of the $40^{th}$ to $60^{th}$ percentile range of values of the illustrative ratio signal of FIG. 7(b) in accordance with some embodiments.

Various methods may be used to filter ratio signal 720 of FIG. 7(b). In some embodiments, the mean of a percentile range is taken as the ratio metric. FIG. 8 shows an illustrative mean of the $40^{th}$ to $60^{th}$ percentile range of values of the illustrative ratio signal of FIG. 7(b) in accordance with some embodiments. For example, the $40^{th}$ to $60^{th}$ percentile range of values of ratio signal 720 may be taken over a 20-second window. Filter settings, such as percentile ranges for obtaining a clipped mean value, and window settings, such as the length of a window, may vary with different embodiments.

Arterial and Venous Ratios

Figure 9:
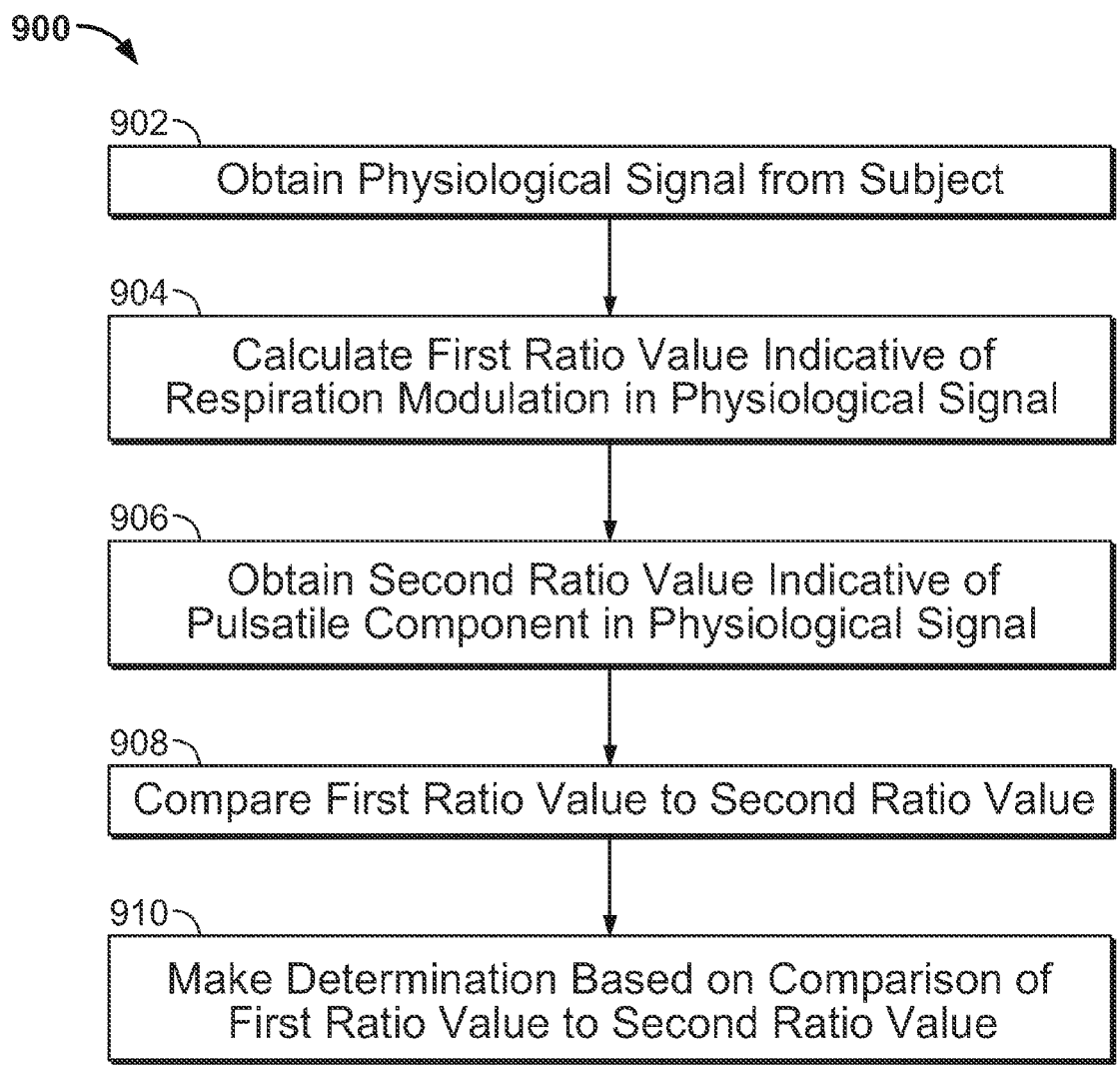
FIG. 9 is a flow chart of illustrative steps for analyzing a physiological signal obtained from a subject in accordance with some embodiments.

A ratio of ratios, calculated for example by performing the steps of FIG. 6 on the physiological signals of FIG. 7(a), may be used to evaluate physiological signals. FIG. 9 is a flow chart 900 of illustrative steps for using a ratio of ratios to analyze a physiological signal obtained from a subject, such as determining whether modulations in the signal are due to respiration or motion, in accordance with some embodiments. FIG. 9 illustrates how to obtain a signal (step 902), how to calculate first and second ratio values based on the signal (steps 904 and 906), and how to process the first and second ratio values to make a determination about the signal or subject (steps 908 and 910). The illustrative steps of flow chart 900 may be performed on the normalized respiration modulation signals of FIG. 7(a), or on any signals acquired at any external or internal body site. The steps of flow chart 900 may be performed by processing equipment such as processor 316 of FIG. 3, microprocessor 48 of FIG. 2, or any suitable processing device. The steps of flow chart 900 may be performed by a digital processing device, or implemented in analog hardware. It will be noted that the steps of flow chart 900 may be performed in any suitable order, and one or more steps may be omitted entirely according to the context and application.

At step 902, a physiological signal is obtained from a subject. The signal may be a PPG signal and may be obtained from any suitable source (e.g., sensor 12 of FIG. 2) using any suitable technique. A sensor from which a signal is obtained may include any of the physiological sensors described herein, or any other sensor. An obtained signal may be signal 402 as shown in FIG. 4(a). An obtained signal may include multiple signals, for example, in the form of a multi-dimensional vector signal or a frequency-multiplexed or time-multiplexed signal. In some embodiments, the physiological signal obtained at step 902 includes two or more PPG signals, which may be measured at two or more respective body sites of a subject.

The physiological signal obtained at step 902 may include first and second physiological signals obtained as input signals. In some embodiments, a first signal is a red PPG signal corresponding to a red wavelength, and a second signal is a PPG signal corresponding to an infrared wavelength. The red and infrared wavelengths may correspond to those used in traditional pulse oximetry, or entirely different wavelengths may be used. In some embodiments, each of the first and second signals includes a cardiac pulsatile component and a baseline modulation component, such as pulsatile component 406 of FIG. 4(a) and baseline modulation component 404 of FIG. 4(b). In some embodiments, first and second signals are obtained by first and second sensors located at approximately the same body site of a subject. In some embodiments, first and second signals are obtained by first and second sensors located at different body sites of a subject. For example, first and second signals included in a plurality of signals may be electronic signals from pulse oximetry sensors located at two different body sites of a subject. It will be noted that the steps of flow diagram 900 may be applied to any number of obtained signals in accordance with the techniques described herein.

At step 904, a first ratio value indicative of a respiration modulation in the physiological signal obtained at step 902 is obtained. The first ratio value may be obtained in conjunction with the obtaining at step 902, or after the physiological signal is obtained at step 902. The first ratio value may be obtained by performing one or more of steps 604-606 as discussed above in relation to FIG. 6. For example, the first parameter mentioned in step 606 may be an amplitude of a respiration-induced baseline modulation in the obtained physiological signal, and the second parameter in step 606 may be a mean amplitude of the respiration-induced baseline modulation. The physiological signal obtained at step 902 may be filtered around a respiration rate in order to derive the respiration-induced baseline modulation, which may represent the modulation of light transmission corresponding to venous blood. The filtering may better distinguish baseline modulations, facilitating the calculation of ratio values. In some embodiments, one or more time derivatives of the obtained physiological signal are used to calculate the first ratio value. Calculation of the first ratio value is further discussed in relation to FIG. 10.

In some embodiments, the first ratio value obtained in step 904 is stored in ROM 52 or RAM 54 (FIG. 1). In some embodiments, the first ratio value obtained in step 904 is processed further or utilized immediately by processor 312 (FIG. 3) for determining information about the subject's physiological condition.

At step 906, a second ratio value indicative of a pulsatile component in the physiological signal obtained at step 902 is obtained. The second ratio value may be obtained in conjunction with the obtaining at step 902, or after the physiological signal is obtained at step 902. The second ratio value may be obtained simultaneously with the first ratio value, or after the first ratio value has been obtained. In some embodiments, the second ratio value is computed from cardiac pulse components of the physiological signal obtained in step 902 in normal oximetry fashion. In some embodiments, one or more time derivatives of the obtained physiological signal are used to calculate the second ratio value. Calculation of the second ratio value is further discussed in relation to FIG. 10.

In some embodiments, the second ratio value obtained in step 906 is stored in ROM 52 or RAM 54 (FIG. 1). In some embodiments, the second ratio value obtained in step 906 is processed further or utilized immediately by processor 312 (FIG. 3) for determining information about the subject's physiological condition.

At step 908, the first ratio value obtained in step 904 is compared to the second ratio value obtained in step 906. The comparison of the first and second ratio values may include deriving a signal quality metric from the first ratio value and the second ratio value. In some embodiments, the signal quality metric is a function, such as a combined ratio, of the first ratio value and the second ratio value. For example, the signal quality metric may be calculated by dividing the first ratio value by the second ratio value. In some embodiments, the signal quality metric is a function of the value of an arterial ratio value (e.g., arterial ratio of ratios) and a venous ratio value (e.g., venous ratio of ratios).

At step 910, a determination is made based on the comparison of the first ratio value to the second ratio value performed in step 908. In some embodiments, the determination is a likelihood that baseline modulations in the physiological signal obtained in step 902 are caused by respiration as opposed to being caused by the subject's movement. A first ratio value that is similar to the second ratio value may be a positive indication of the modulations being due to respiration, assuming that minimal oxygen demand takes place at the site (e.g., finger) where the physiological signal is obtained and that the arterial and venous blood therefore have very similar values. In some embodiments, the first ratio value is a venous RoR and the second ratio value is an arterial RoR. It is known that an RoR of unity may be an indication of a movement artifact. Hence, the further the venous RoR and the arterial RoR are from unity and the more similar the venous RoR and the arterial RoR are to each other, the higher the confidence in the computed arterial and venous oxygen saturations.

In some embodiments, the determination made at step 910 is based on a difference between a signal quality metric, such as the signal quality metric derived in step 908, and a threshold value. The threshold value may be retrieved from a look-up table stored in memory, such as ROM 52 or RAM 54 (FIG. 1), or external storage.

In some embodiments, the threshold value is a finger oxygen usage measure derived from a long-term difference between respiration and pulsatile modulations in data collected from the subject over time. The finger oxygen usage measure may be expected to be relatively constant over time even as arterial SpO2 changes. A physiological signal, such as a PPG signal, obtained at a subject's finger is useful for determining whether a modulation in the signal is due to respiration or movement because the oxygen content of the arterial and venous blood at the finger may be very similar due to oxygen demand at the fingertip being relatively small. Any sudden deviations of a signal quality metric, such as the signal quality metric derived in step 908, from the established finger oxygen usage measure may indicate that modulations in the physiological signal obtained in step 902 are due to the subject's motion. In other words, a short term finger oxygen usage measure that is similar to the long term average may indicate that recent venous/baseline modulations are likely due to the subject's respiration.

In some embodiments, a pulse oximetry system includes an indication of the first ratio value calculated in step 904 relative to the second ratio value calculated in step 906. The indication may be of a difference between a threshold value and a combined ratio of ratios. The combined ratio of ratios may include a function of a first ratio of ratios (e.g., venous RoR) and a second ratio of ratios (e.g., arterial RoR). An indicator, which may appear on display 28 of FIG. 1 or display 20 of FIG. 2, or any other display that is communicatively coupled to the pulse oximetry system, may indicate whether baseline modulation in at least one of the first and second wavelength components (e.g., red and IR wavelength components) is due to respiration or motion of the subject. The indicator may indicate that baseline modulation in at least one of the first and second wavelength components is due to respiration of the subject when there are small deviations of the combined ratio of ratios from a threshold value. The indicator may indicate that baseline modulation in at least one of the first and second wavelength components is due to motion of the subject when there are large deviations of the combined ratio of ratios from the threshold value. In some embodiments, the indicator includes a visible or audible alarm that is triggered when a baseline modulation in at least one of the first and second wavelength components is due to motion of the subject.

Figure 10:
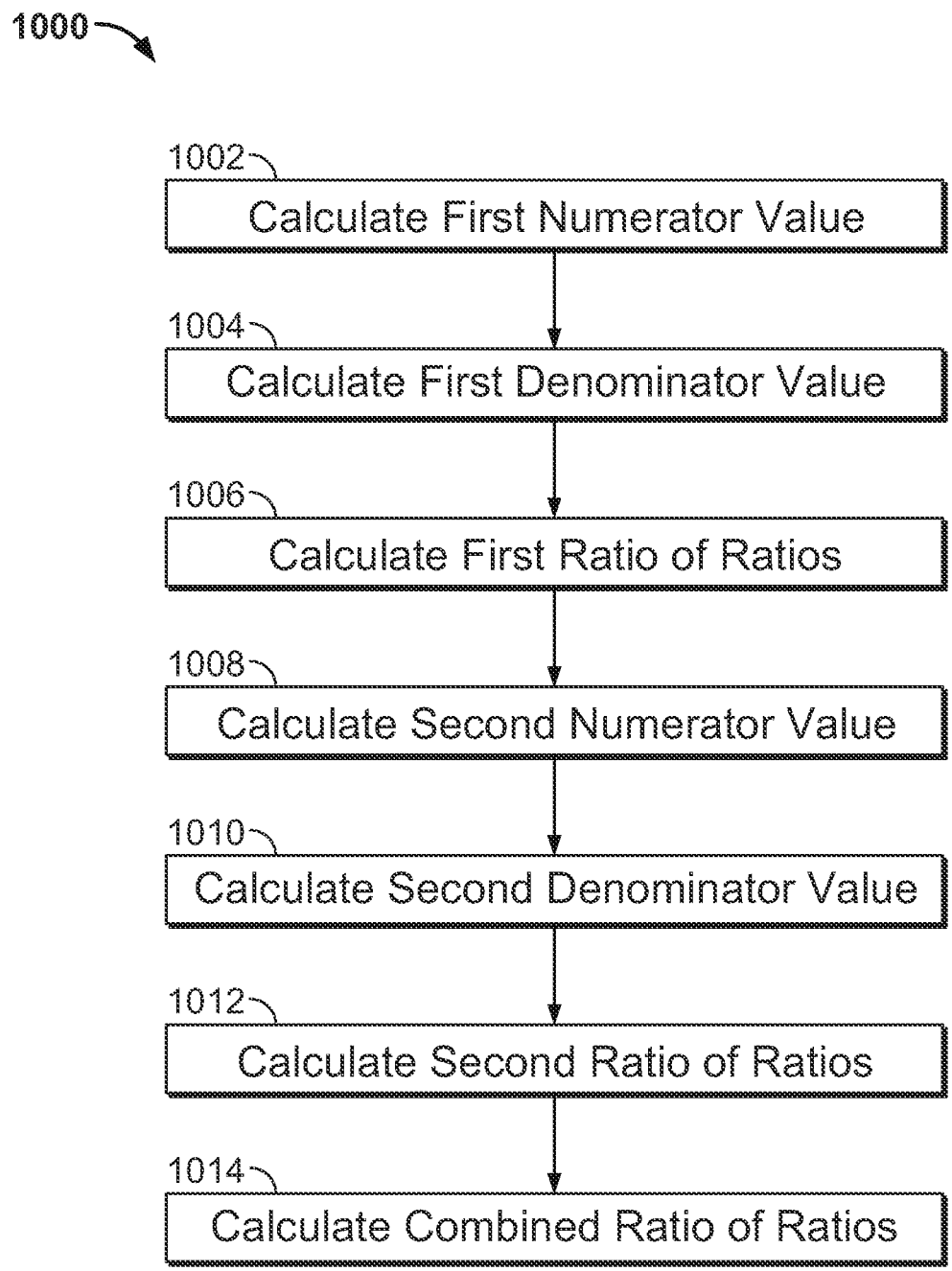
FIG. 10 is a flow chart of illustrative steps for analyzing a physiological signal obtained from a subject in accordance with some embodiments.

Calculation of the first and second ratio values of FIG. 9 is further discussed with respect to FIG. 10. FIG. 10 is a flow chart 1000 of illustrative steps for using ratios to analyze a physiological signal obtained from a subject in accordance with some embodiments. FIG. 10 illustrates how to calculate a first ratio of ratios (steps 1002, 1004, and 1006) and a second ratio of ratios (steps 1008, 1010, and 1012), and then how to calculate a combined ratio of ratios (step 1014). The illustrative steps of flow chart 1000 may be performed as part of or in addition to some of the illustrative steps of flow chart 900, and may be performed on any signals acquired at any external or internal body site. The steps of flow chart 1000 may be performed by processing equipment such as processor 316 of FIG. 3, microprocessor 48 of FIG. 2, or any suitable processing device. The steps of flow chart 1000 may be performed by a digital processing device, or implemented in analog hardware. It will be noted that the steps of flow chart 1000 may be performed in any suitable order, and one or more steps may be omitted entirely according to the context and application.

At step 1002, a first numerator value is calculated from a first respiratory modulation signal derived from a physiological signal of a first wavelength. The physiological signal of a first wavelength may be, for example, a PPG signal corresponding to a red wavelength. The first numerator may be computed by dividing an amplitude of the first respiratory modulation by a mean baseline value of the first respiratory modulation. In some embodiments, the amplitude is a mean peak to trough value of the first respiratory modulation over a window of time. The time window may vary based on the respiration rate of the patient. The mean baseline may be a low-pass filtered version of the respiratory modulation signal. Methods of calculating amplitudes and mean baseline values are discussed in more detail above in connection with FIG. 6. In some embodiments, the first numerator value calculation excludes points where the baseline of the first respiratory modulation signal is zero.

At step 1004, a first denominator value is calculated from a second respiratory modulation signal derived from a physiological signal of a second wavelength. The physiological signal of a second wavelength may be, for example, a PPG signal corresponding to an infrared wavelength. The second numerator is computed by dividing an amplitude of the second respiratory modulation by a baseline value of the second respiratory modulation. In some embodiments, the amplitude of the second respiratory signal is a mean peak to trough value signal over a window of time. The time window may vary based on the respiration rate of the patient. In some embodiments, the second denominator value excludes points where the baseline value is zero.

At step 1006, a first ratio of ratios is calculated using the first numerator value obtained at step 1002 and the first denominator value obtained at step 1004. For example, the first numerator value may be divided by the first denominator value to obtain the first ratio of ratios. In some embodiments, calculating the first ratio of ratios involves calculating a logarithmic term. For example, the ratio of ratios may be the quotient of the logarithm of the first numerator and the logarithm of the first denominator. The first ratio of ratios may be indicative of the oxygen saturation of the subject's venous blood.

At step 1008, a second numerator value is calculated by dividing a first amplitude of a first pulsatile component in a first wavelength component of the obtained physiological signal by a first mean amplitude of the first pulsatile component. The first wavelength component may be, for example, a component of a PPG signal corresponding to a red wavelength.

At step 1010, a second denominator value is calculated by dividing a second amplitude of a second pulsatile component in a second wavelength component of the obtained physiological signal by a second mean amplitude of the second pulsatile component. The second wavelength component may be, for example, a component of a PPG signal corresponding to an IR wavelength.

At step 1012, a second ratio of ratios is calculated using the second numerator value obtained in step 1008 and the second denominator value obtained in step 1010. For example, the second numerator value may be divided by the second denominator value to obtain the second ratio of ratios. In some embodiments, calculating the second ratio of ratios involves calculating a logarithmic term. For example, the natural logarithm of the quotient of the second numerator value and the second denominator value may be calculated to obtain the second ratio of ratios. The second ratio of ratios may be indicative of the oxygen saturation of the subject's arterial blood.

At step 1014, a combined ratio of ratios, which includes comparing the first ratio of ratios calculated in step 1006 and the second ratio of ratios calculated in step 1012, is calculated. For example, the combined ratio of ratios may be calculated by dividing the first ratio of ratios by the second ratio of ratios. In some embodiments, the combined ratio of ratios is a function of the value of an arterial ratio of ratios and a venous ratio of ratios. For example, the combined ratio of ratios may be calculated by dividing the natural logarithm of the arterial ratio of ratios by the natural logarithm of the venous ratio of ratios, as in equation (9), discussed in relation to FIG. 6.

Figure 11:
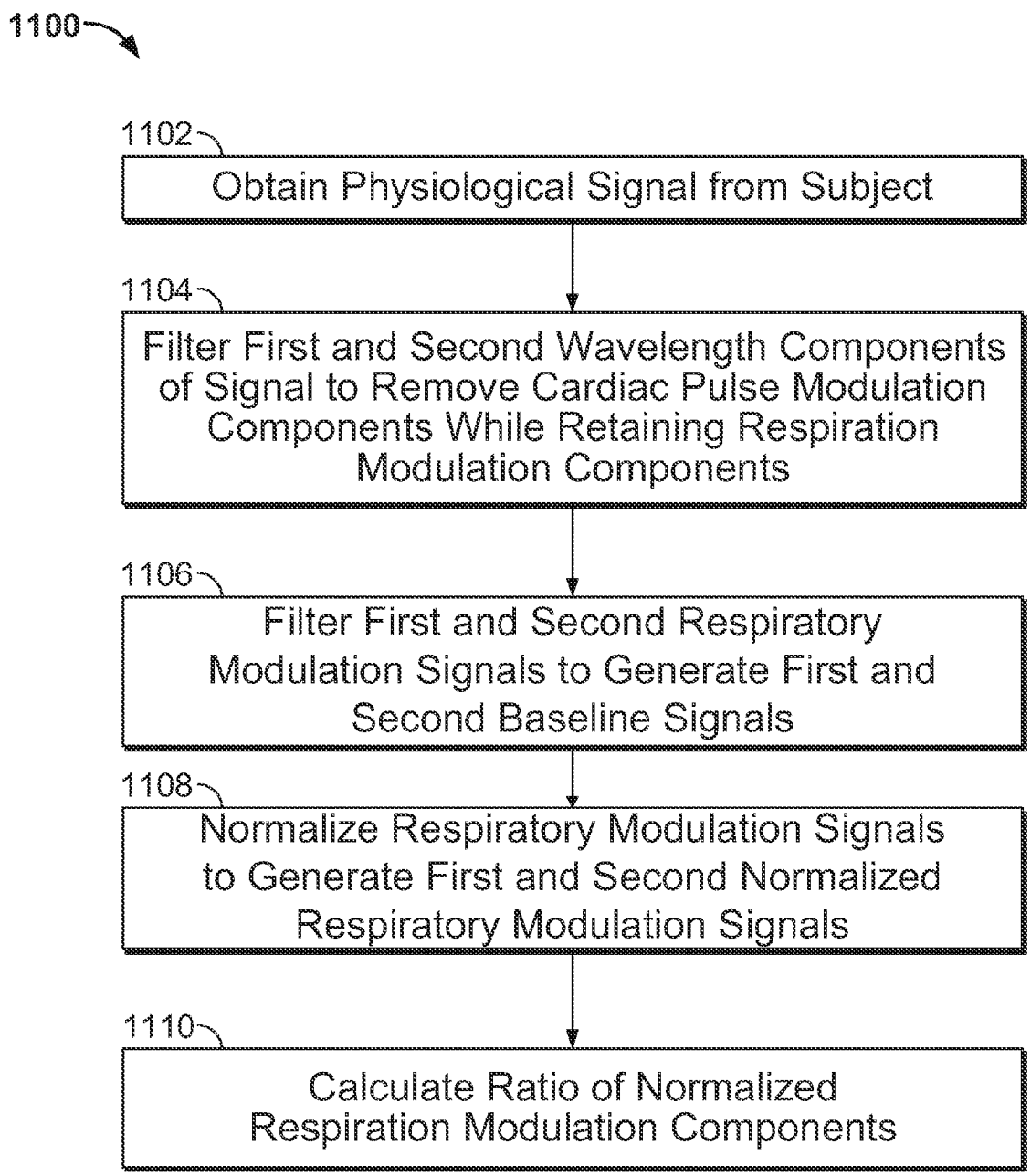
FIG. 11 is a flow chart of illustrative steps for analyzing a physiological signal obtained from a subject in accordance with some embodiments.

FIG. 11 is a flow chart 1100 illustrating steps for a ratio method of analyzing a physiological signal obtained from a subject, where the respiration modulation components of the obtained physiological signal are normalized in accordance with some embodiments. In particular, FIG. 11 illustrates how to obtain a signal (step 1102), how to filter first and second wavelength components (steps 1104 and 1106), and then how to normalize respiration modulation components and use them to calculate a ratio (steps 1108 and 1110). The illustrative steps of flow chart 1100 may be performed to obtain the normalized respiration modulation signals of FIG. 7(*a*) and may be performed as part of, in addition to, or instead of some of the illustrative steps of flow charts 900 or 1000. The illustrative steps of flow chart 1100 may be performed on any signals acquired at any external or internal body site. The steps of flow chart 1100 may be performed by processing equipment such as processor 316 of FIG. 3, microprocessor 48 of FIG. 2, or any suitable processing device. The steps of flow chart 1100 may be performed by a digital processing device, or implemented in analog hardware. It will be noted that the steps of flow chart 1100 may be performed in any suitable order, and one or more steps may be omitted entirely according to the context and application.

At step 1102, a physiological signal is obtained from a subject. The signal may be a PPG signal and may be obtained from any suitable source (e.g., sensor 12 of FIG. 2) using any suitable technique. A sensor from which a signal is obtained may include any of the physiological sensors described herein, or any other sensor. An obtained signal may be signal 402 as shown in FIG. 4(*a*). An obtained signal may include multiple signals, for example, in the form of a multi-dimensional vector signal or a frequency-multiplexed or time-multiplexed signal. In some embodiments, the physiological signal obtained at step 1102 includes two or more PPG signals, which may be measured at two or more respective body sites of a subject.

The physiological signal obtained at step 1102 may include first and second physiological signals obtained as input signals. In some embodiments, a first signal is a red PPG signal corresponding to a red wavelength, and a second signal is a PPG signal corresponding to an infrared wavelength. The red and infrared wavelengths may correspond to those used in traditional pulse oximetry, or entirely different wavelengths may be used. In some embodiments, each of the first and second signals includes a cardiac pulsatile component and a baseline modulation component, such as pulsatile component 406 of FIG. 4(*a*) and baseline modulation component 404 of FIG. 4(*b*). In some embodiments, first and second signals are obtained by first and second sensors located at approximately the same body site of a subject. In some embodiments, first and second signals are obtained by first and second sensors located at different body sites of a subject. For example, first and second signals included in a plurality of signals may be electronic signals from pulse oximetry sensors located at two different body sites of a subject. It will be noted that the steps of flow diagram 1100 may be applied to any number of obtained signals in accordance with the techniques described herein.

At step 1104, first and second wavelength components of the physiological signal obtained at step 1102 are filtered to remove cardiac pulse modulation components while retaining respiration modulation components—these are the first and second respiratory modulation signals. In some embodiments, the physiological signal obtained at step 902 is filtered based on a respiration rate in order to derive the respiration-induced baseline modulation components. For example, a physiological signal may be low-pass filtered at 0.5 Hz to remove cardiac modulations while retaining respiratory modulations. The retained modulation represents the modulation of light transmission corresponding to venous blood.

At step 1106, the first and second respiratory modulation signals are filtered to generate first and second baseline signals. In some embodiments, baseline signals are generated by low-pass filtering the first and second respiratory modulation signals at a frequency below the respiration rate. For example, the first and second respiratory modulation signals may be low-pass filtered at 0.1 Hz.

At step 1108, respiratory modulation signals obtained in step 1106 are normalized to generate first and second normalized respiratory modulation signals. Normalized signals are illustrated in plot 700 of FIG. 7(*a*). In some embodiments, a normalized signal is computed by taking the difference between a respiratory modulation signal and its baseline signal and then dividing this difference by the baseline signal.

At step 1110, a ratio of normalized respiration modulation components is calculated. The ratio may be calculated by dividing the first normalized respiratory modulation signal by the second normalized respiratory modulation signal or vice versa. In another embodiment, the ratio is calculated by dividing the logarithm of the first normalized respiratory modulation signal by the second normalized respiratory modulation signal. The ratio may be calculated by processing equipment such as processor 316 of FIG. 3, microprocessor 48 of FIG. 2, or any suitable processing device. The calculated ratio may be indicative of whether motion of the subject has caused at least one of the first and second respiration modulation components. Ratios of normalized respiration modulation components are illustrated in and discussed above in relation to FIGS. 7(*b*)-(*c*) and FIG. 8.

In some embodiments, respiration modulation components from a PPG signal, such as the physiological signal obtained from a subject in any of steps 602, 902, and 1102, may be further identified and evaluated by transforming the respiration modulation components using a continuous wavelet transform. Information derived from the transform of the respiration modulation components (i.e., in wavelet space) may be used to provide measurements of one or more physiological parameters, or to determine whether modulations in the signal are due to respiration or motion.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \quad (10)$$

where ψ*(t) is the complex conjugate of the wavelet function ψ(t), a is the dilation parameter of the wavelet and b is the location parameter of the wavelet. The transform given by equation (10) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, and phase, among others, may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \tag{11}$$

where '||' is the modulus operator. The scalogram may be resealed for useful purposes. One common resealing is defined as $$S_R(a, b) = \frac{|T(a, b)|^2}{a} \tag{12}$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane is labeled a "maxima ridge."

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of resealing including, but not limited to, the original unsealed wavelet representation, linear resealing, any power of the modulus of the wavelet transform, or any other suitable resealing. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram."

A scale, which may be interpreted as a representative temporal period, may be converted to a characteristic frequency of the wavelet function. The characteristic frequency associated with a wavelet of arbitrary a scale is given by $$f = \frac{f_c}{a} \tag{13}$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \tag{14}$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case the Morlet wavelet can be written in a simpler form as $$\psi(t) = \frac{1}{\pi^{1/4}} e^{i2\pi f_0 t} e^{-t^2/2} \tag{15}$$

This wavelet is a complex wave within a scaled Gaussian envelope. While both definitions of the Morlet wavelet are included herein, the function of equation (15) is not strictly a wavelet as it has a non-zero mean (i.e., the zero frequency term of its corresponding energy spectrum is non-zero). However, it will be recognized by those skilled in the art that equation (15) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 12B:
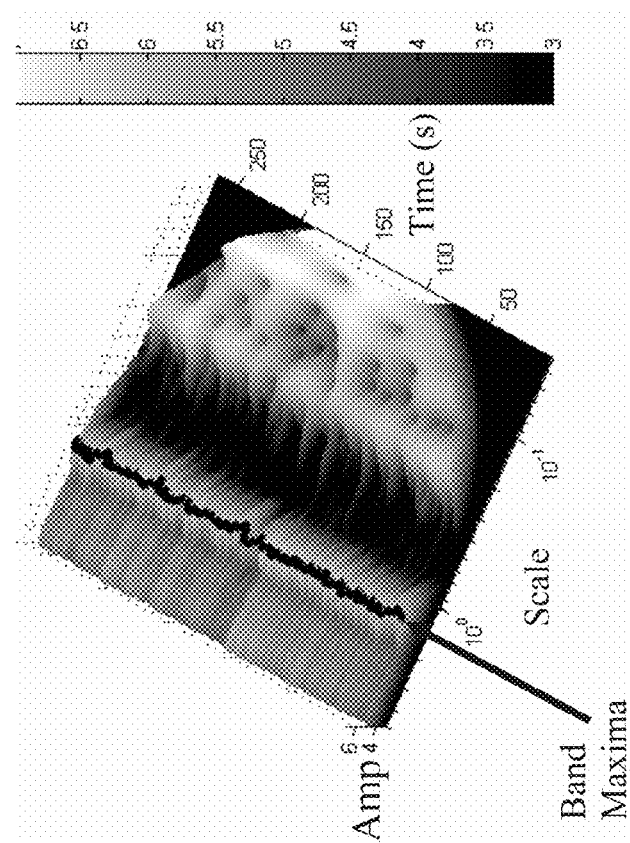
FIGS. 12(a) and 12(b) show illustrative views of a scalogram derived from a PPG signal in accordance with some embodiments.
Figure 12A:
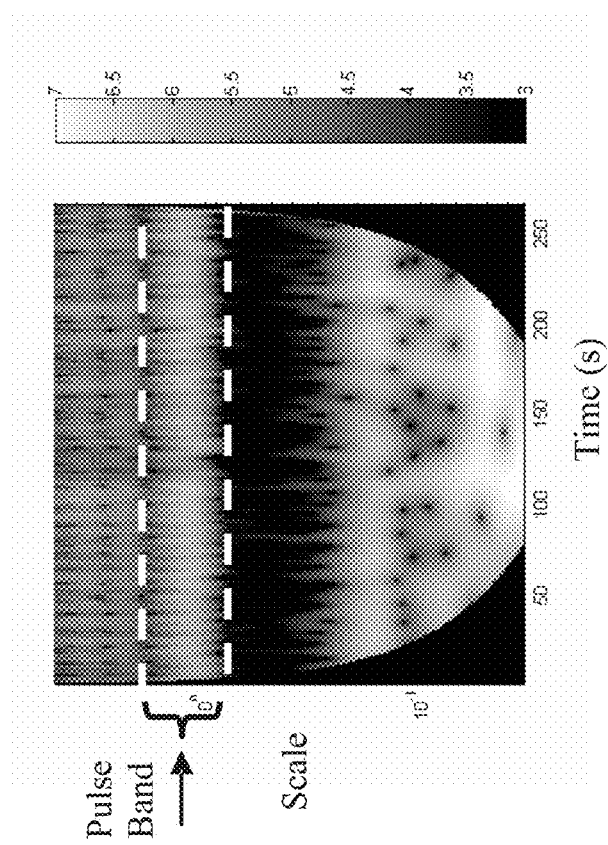

Pertinent repeating features in a signal give rise to a time-scale band in wavelet space or a resealed wavelet space. For example, the pulse component of a PPG signal produces a dominant band in wavelet space at or around the pulse frequency. FIGS. 12(a) and (b) show two views of an illustrative scalogram derived from a PPG signal in accordance with some embodiments. The figures show an example of the band caused by the pulse component in such a signal. The pulse band is located between the dashed lines in the plot of FIG. 12(a). The band is formed from a series of dominant coalescing features across the scalogram. This can be clearly seen as a raised band across the transform surface in FIG. 12(b) located within the region of scales indicated by the arrow in the plot (corresponding to 60 beats per minute). The maxima of this band with respect to scale form a ridge. The locus of the ridge is shown as a black curve on top of the band in FIG. 12(b). By employing a suitable resealing of the scalogram, such as that given in equation (12), the ridges found in wavelet space may be related to the instantaneous frequency of the signal. In this way, the pulse rate is obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 12C:
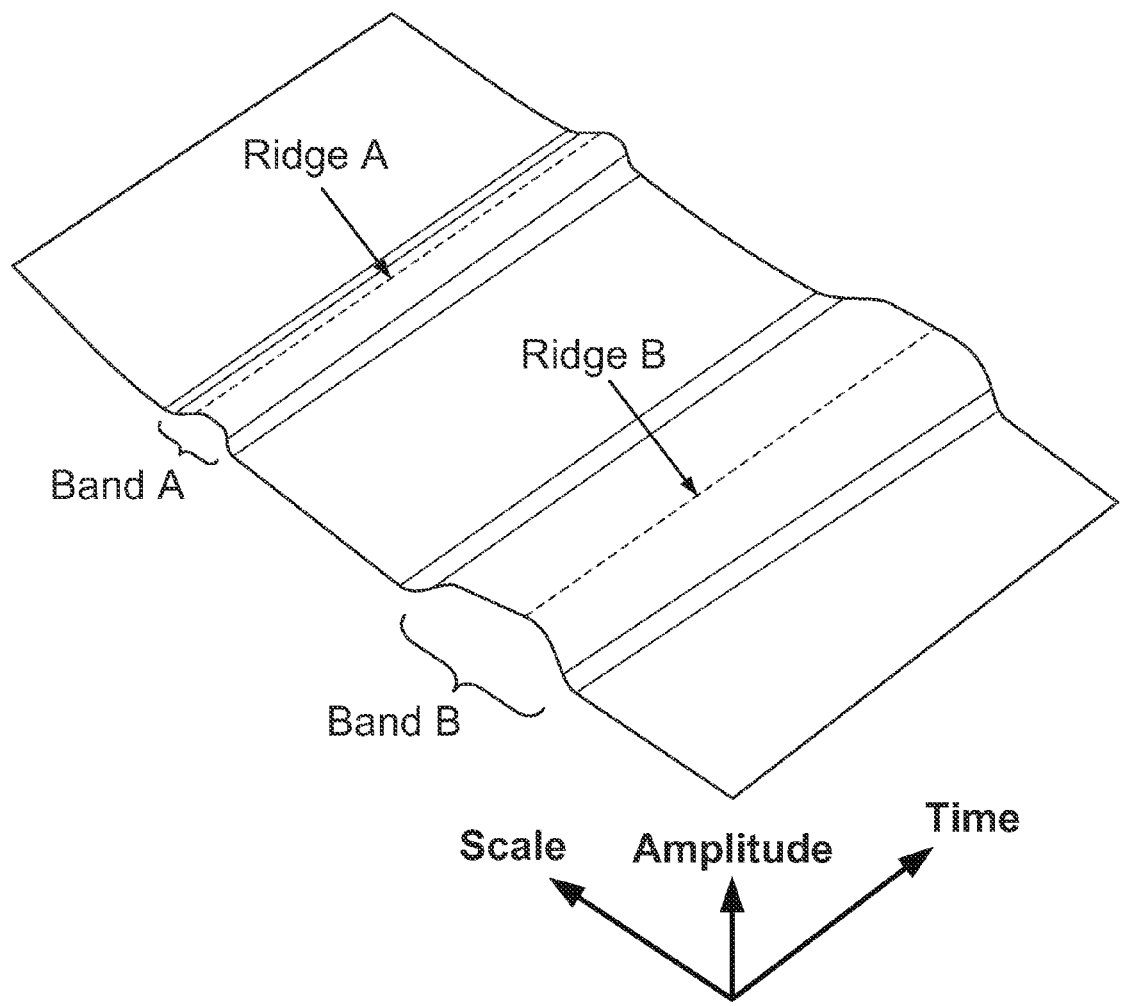
FIG. 12(c) shows an illustrative scalogram derived from a signal containing two pertinent components in accordance with some embodiments.
Figure 12D:
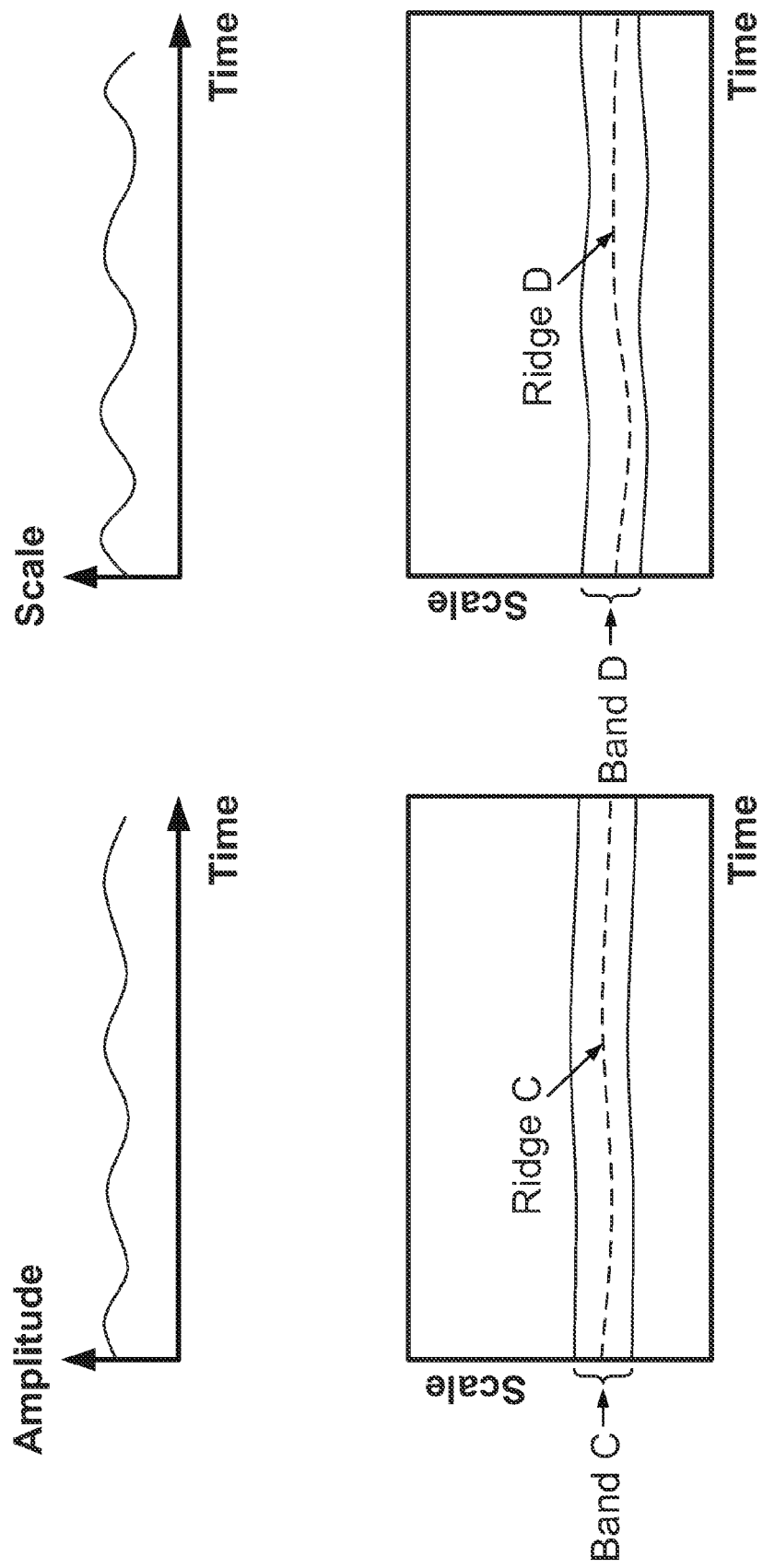
FIG. 12(d) shows an illustrative schematic of signals associated with FIG. 12(c) and further wavelet decomposition thereof in accordance with some embodiments.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary, varying in scale, amplitude, or both over time. FIG. 12(c) shows an illustrative schematic of a wavelet transform of a signal containing two pertinent components leading to two bands in the transform space in accordance with some embodiments. These bands are labeled band A and band B on the three-dimensional schematic of the wavelet surface. In some embodiments, the band ridge is defined as the locus of the peak values of these bands with respect to scale. For purposes of discussion, it may be assumed that band B contains the signal information of interest. This will be referred to as the "primary band." In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A is followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 12(d) show a schematic of the RAP and RSP signals associated with ridge A in FIG. 12(c). Below these RAP and RSP signals are schematics of a further wavelet decomposition of these newly derived signals. This secondary wavelet decomposition allows for information in the region of band B in FIG. 12(c) to be made available as band C and band D. The ridges of bands C and D may serve as instantaneous time-scale characteristic measures of the signal components causing bands C and D. This technique, which will be referred to herein as secondary wavelet feature decoupling (SWFD), allows information concerning the nature of the signal components associated with the underlying physical process causing the primary band B (FIG. 12(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In some embodiments, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \tag{16}$$

which may also be written as:

$$x(t) = \frac{1}{C_g} \int_{-\infty}^{\infty} \int_0^{\infty} T(a,b) \psi_{a,b}(t) \frac{da\,db}{a^2} \tag{17}$$

where $C_g$ is a scalar value known as the admissibility constant. It is wavelet type dependent and may be calculated from:

$$C_g = \int_0^{\infty} \frac{|\hat{\psi}(f)|^2}{f} df \tag{18}$$

Figure 12E:
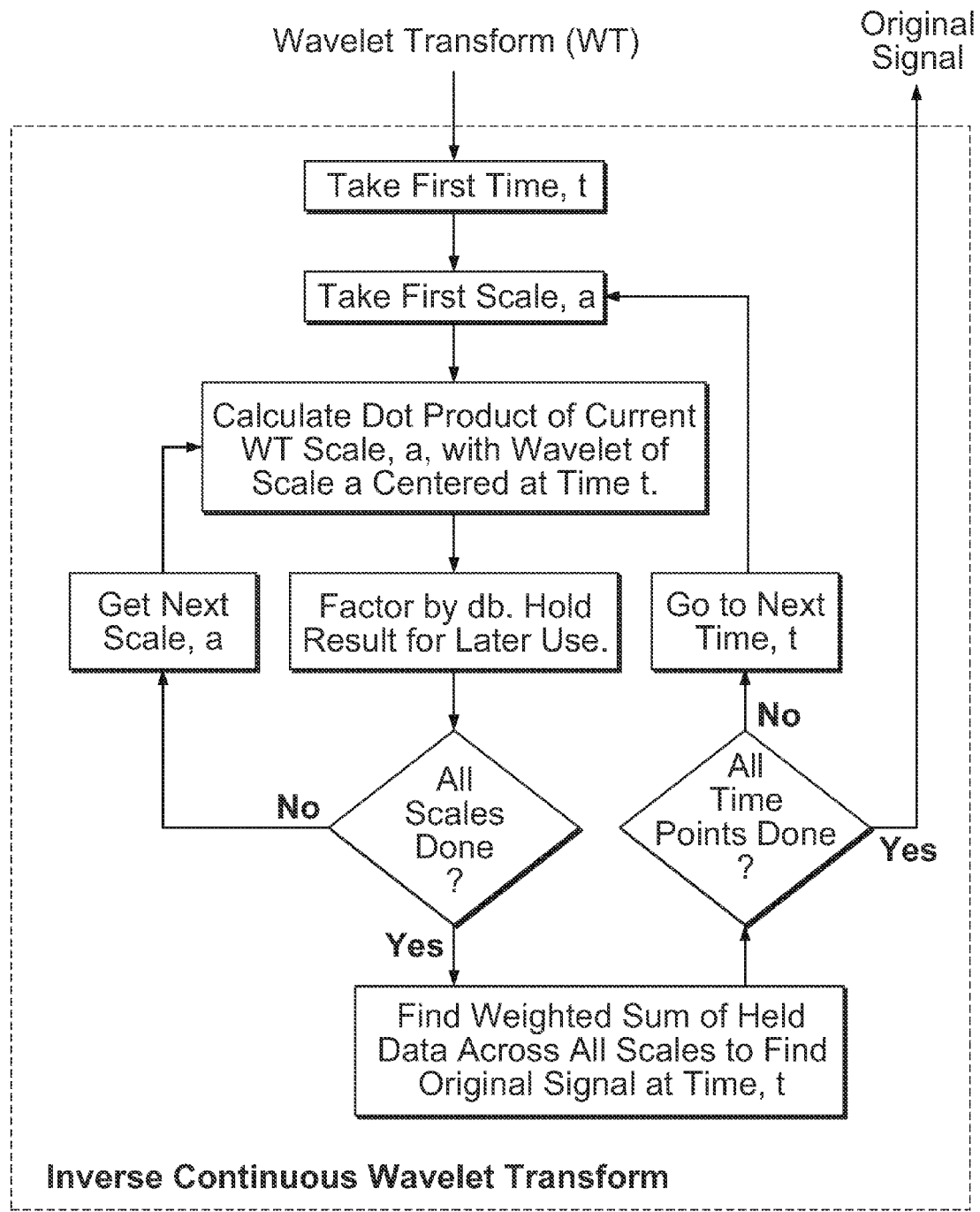
FIGS. 12(e) and 12(f) are flow charts of illustrative steps involved in performing an inverse continuous wavelet transform in accordance with some embodiments.
Figure 12F:
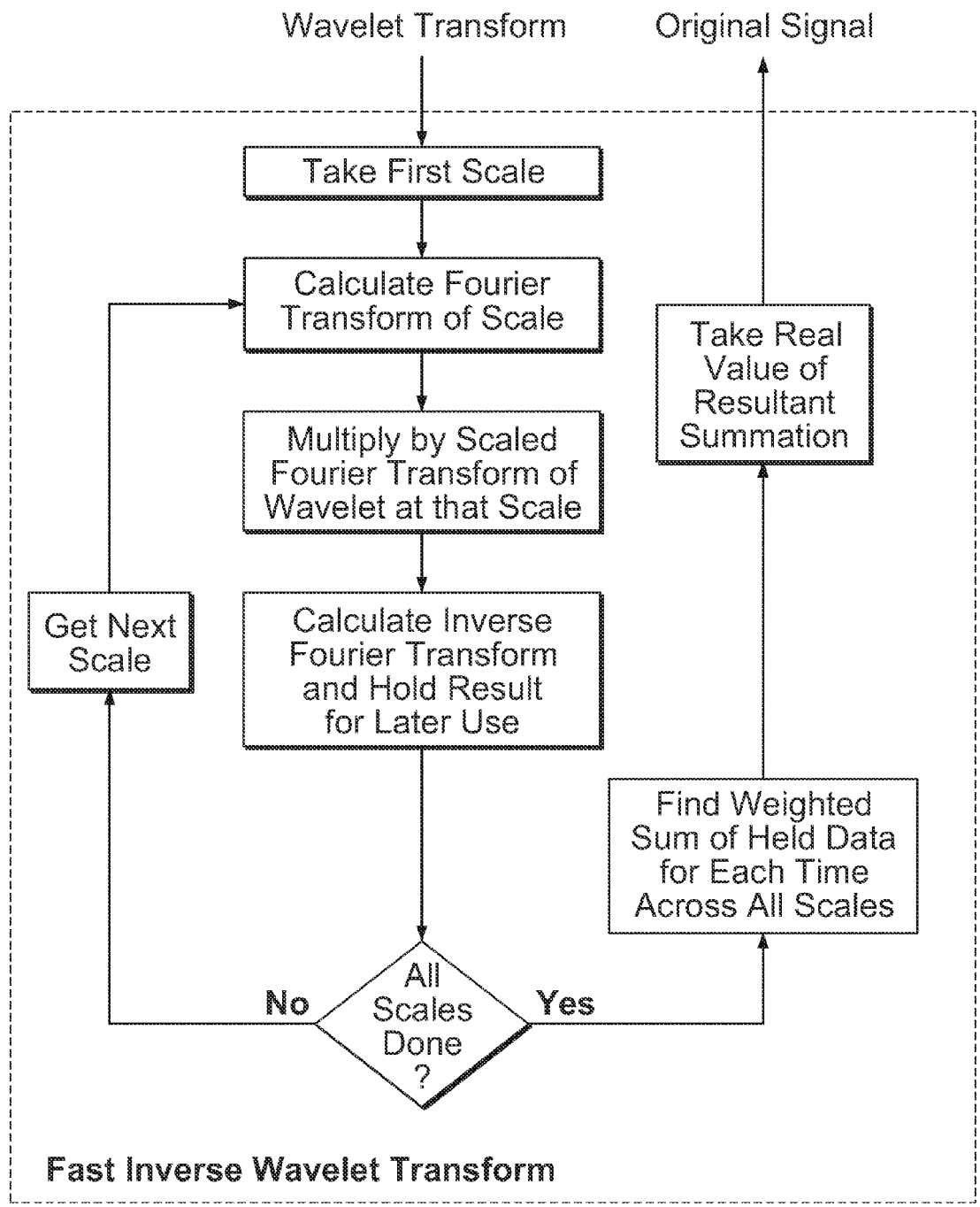

FIG. 12(e) is a flow chart of illustrative steps that may be taken to perform an inverse continuous wavelet transform in accordance with the above discussion. An approximation to the inverse transform may be made by considering equation (16) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 12(f) is a flow chart of illustrative steps that may be taken to perform an approximation of an inverse continuous wavelet transform. It will be understood that any other suitable technique for performing an inverse continuous wavelet transform may be used in accordance with the present disclosure.

Transformed Respiration Modulation Ratios

Figure 13:
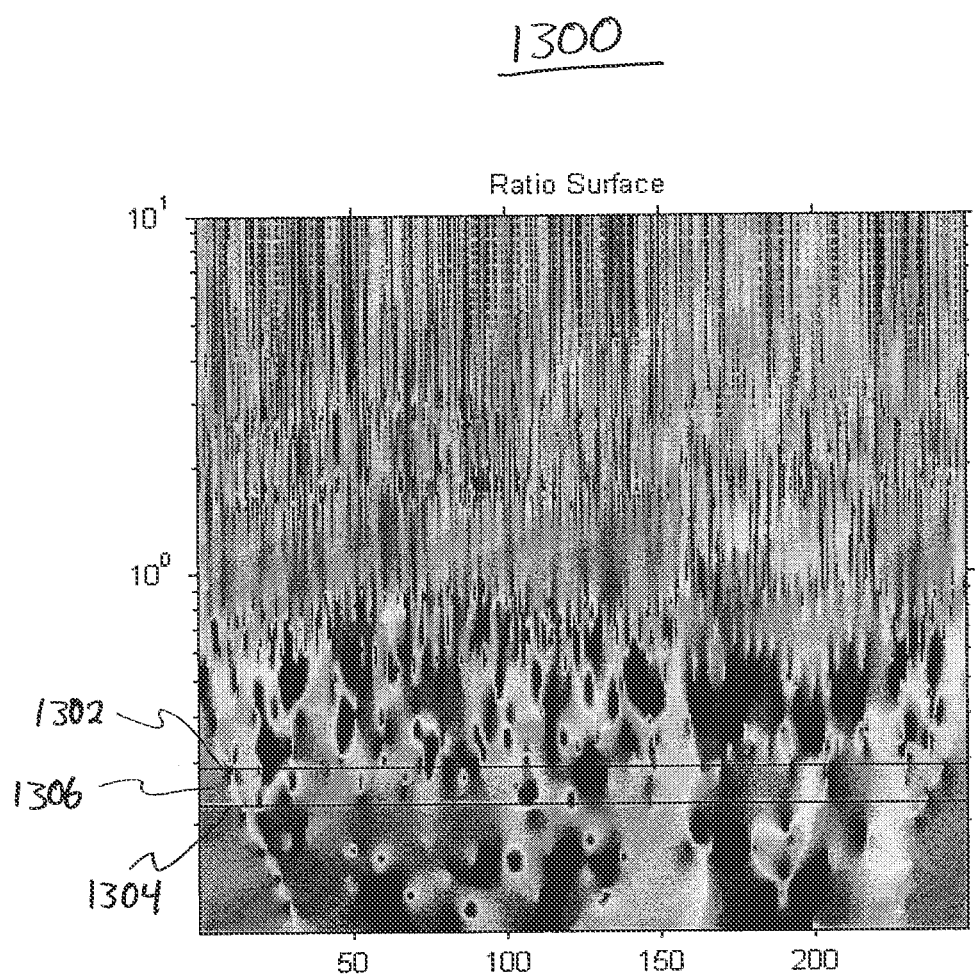
FIG. 13 shows an illustrative wavelet transform ratio surface of the normalized respiration modulation signals of FIG. 7(a) in accordance with some embodiments.

A wavelet transform of physiological signals (e.g., PPG signals), such as the continuous wavelet transform discussed in relation to FIGS. 12(a)-(f), may be used to generate a wavelet transform ratio surface for further analysis of the respiration modulation components. FIG. 13 shows an illustrative wavelet transform ratio surface 1300 of the physiological signals of the type depicted in FIG. 4(a) in accordance with some embodiments. Wavelet transform ratio surface 1300 is obtained by applying a continuous wavelet transform to first and second physiological signals corresponding to first and second wavelengths as discussed further in relation to FIG. 14. In some embodiments, these signals correspond to the red and infrared PPG signals used in traditional pulse oximetry, but the methods described herein may be applied to other types of signals corresponding to other wavelengths. A region of interest 1306 is defined within lines 1302 and 1304 drawn across wavelet transform ratio surface 1300. Regions of interest are discussed further in relation to FIGS. 14 and 16.

In some embodiments, data representing a wavelet transform ratio surface is stored in RAM or memory internal to processor 312 as any suitable three-dimensional data structure such as a three-dimensional array that represents the wavelet transform ratio surface as energy levels in a time-scale plane. Any other suitable data structure may be used to store data representing a wavelet transform ratio surface.

Figure 14:
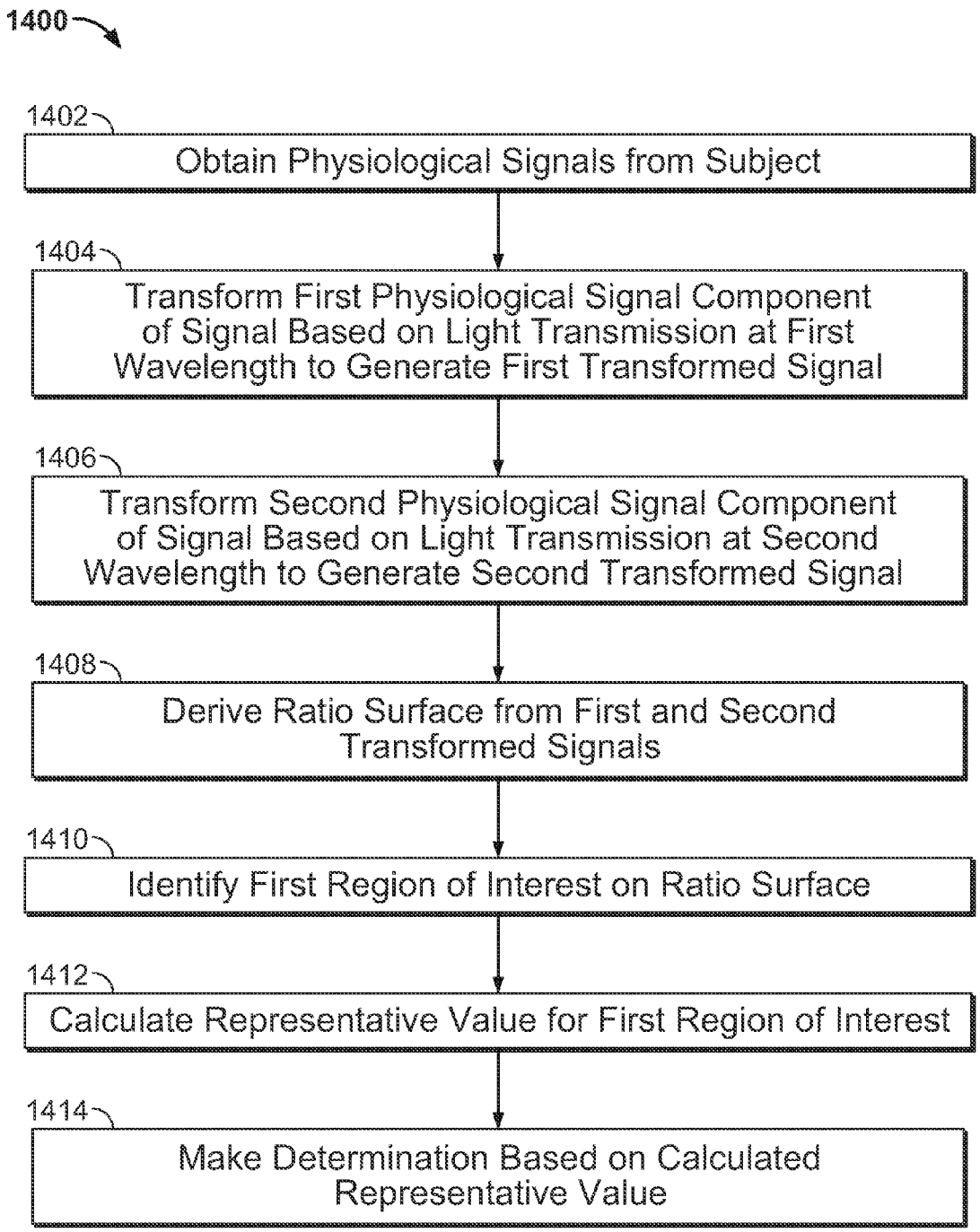
FIG. 14 is a flow chart of illustrative steps for analyzing a respiration modulation signal obtained from a subject in accordance with some embodiments.

A transform technique may be used with a ratio of signal components to determine the extent to which signal quality is degraded by motion artifact. A determination of signal quality using a transform technique may be used to confirm a determination of signal quality made using a non-transform technique, such as the steps described in FIGS. 9-11. FIG. 14 is a flow chart 1400 of illustrative steps for using transforms and ratios to analyze a physiological signal obtained from a subject in accordance with some embodiments. FIG. 14 illustrates how to obtain first and second physiological signals (step 1402), how to transform first and second physiological signals to derive a ratio surface (steps 1404, 1406, and 1408), and then how to identify and analyze a region of interest on the ratio surface (steps 1410, 1412, and 1414). The steps of flow chart 1400 may be performed by processing equipment such as processor 316 of FIG. 3, microprocessor 48 of FIG. 2, or any suitable processing device. The steps of flow chart 1400, including the calculations associated with the continuous wavelet transforms of the present disclosure as well as the calculations associated with any suitable interrogations of the transforms, may be performed by a digital processing device, or implemented in analog hardware. It will be noted that the steps of flow chart 1400 may be performed in any suitable order, and one or more steps may be omitted entirely according to the context and application.

At step 1402, first and second physiological signals are obtained from a subject. The first and second physiological signals may be red and infrared PPG signals and may be obtained from any suitable source (e.g., sensor 12 of FIG. 2) using any suitable technique. A sensor from which a signal is obtained may include any of the physiological sensors described herein, or any other sensor. An obtained signal may be signal 402 as shown in FIG. 4(a). An obtained signal may include multiple signals, for example, in the form of a multi-dimensional vector signal or a frequency-multiplexed or time-multiplexed signal. In some embodiments, the physiological signal obtained at step 1402 includes two or more PPG signals, which may be measured at two or more respective body sites of a subject.

The physiological signal obtained at step 1402 may include first and second physiological signals obtained as input signals. In some embodiments, a first signal is a red PPG signal, and a second signal is an infrared PPG signal In some embodiments, each of the first and second physiological signals includes a pulsatile component and a baseline modulation component, such as pulsatile component 406 of FIG. 4(a) and baseline modulation component 404 of FIG. 4(b). It will be noted that the steps of flow diagram 1400 may be applied to any number of obtained signals in accordance with the techniques described herein.

At step 1404, a first physiological signal, corresponding to a first wavelength, is transformed to generate a first transformed signal. In some embodiments, the transformation of step 1404 is applied to a derivative of the first physiological signal. In some embodiments, the transformation of step 1404 is a wavelet transform, such as a continuous wavelet transform, as discussed above in relation to FIGS. 12(a)-(b). In some embodiments, the first transformed signal calculated in step 1404 is stored in ROM 52 or RAM 54 (FIG. 1). In some embodiments, the first transformed signal calculated in step 1404 is processed further or utilized immediately by processor 312 (FIG. 3) for determining information about the subject's physiological condition.

At step 1406, a second physiological signal, corresponding to a second wavelength, is transformed to generate a second transformed signal. In some embodiments, the transform is applied to the derivative of the second physiological signal, rather than the signal itself. The second transformed signal may be calculated simultaneously with the first transformed signal, or after the first transformed signal has been calculated. In some embodiments, the transformation of step 1406 is a wavelet transform, such as a continuous wavelet transform, as discussed above in relation to FIGS. 12(a)-(b). In some embodiments, the transformation of step 1406 is applied to time derivatives of the second respiration signal component.

In some embodiments, the second transformed signal calculated in step 1406 is stored in ROM 52 or RAM 54 (FIG. 1). In some embodiments, the second transformed signal calculated in step 1406 is processed further or utilized immediately by processor 312 (FIG. 3) for determining information about the subject's physiological condition.

At step 1408, a ratio surface is derived from the first and second transformed signals obtained at steps 1404 and 1406, respectively. In some embodiments, the ratio surface is derived by dividing the first transformed signal by the second transformed signal, or vice-versa. In some embodiments, a ratio surface, such as the ratio surface 1300 shown in FIG. 13, is derived by calculating a modulus of the first transformed signal and a modulus of the second transformed signal and dividing the first modulus by the second modulus. In embodiments where the transform produces a complex signal, the modulus is defined as:

$$|T(a,b)| = \sqrt{T(a,b)_{real}^2 + T(a,b)_{imaginary}^2}$$

In some embodiments, deriving the ratio surface involves normalizing the first and second physiological signals by a value. For example, the respective magnitude of each of the first and second physiological signals may be divided by the respective minimum, maximum, mean, DC component, or standard deviation computed over a time window of the first and second physiological signals.

At step 1410, a first region of interest on the ratio surface derived in step 1408 is identified. In some embodiments, the first region of interest, such as region of interest 1306 of FIG. 13, is related to a respiration rate. In some embodiments, the first region of interest is an area of the ratio surface having values close to an expected venous saturation ratio value. In some embodiments, such an area of the ratio surface is used as a confidence metric to improve existing respiration rate detection by weighting the output of a respiration rate algorithm according to the likelihood of the area being affected by motion.

At step 1412, a representative value is calculated for a first region of interest. In some embodiments, calculating a representative value involves filtering instantaneous values of the ratio surface. For example, a median value over a specified time interval of a mean value across the first region of interest identified at step 1410 may be calculated, as discussed further in relation to FIG. 15. In some embodiments, an estimated rate of respiration of the subject is calculated based on an identified region of the ratio surface having values close to an expected venous saturation ratio value. Such a calculated respiration rate may be used in conjunction with other methods, for example ridge tracking, to detect a baseline breathing band.

At step 1414, a determination is made based on the representative value calculated at step 1412. In some embodiments, the determination is whether the representative value calculated at step 1412 for the first region of interest identified at step 1410 indicates respiration or motion of the subject. In some embodiments, a representative value for arterial oxygen saturation of the subject is obtained (e.g., in normal oximetry fashion), and the representative value for arterial oxygen saturation is compared to the representative value for the first region of interest on the ratio surface. Similarity between the representative value for arterial oxygen saturation of the subject and the representative value for the first region of interest on the ratio surface may be indicative of baseline modulations in the first and second respiration signal components being due to respiration of the subject.

In some embodiments, determining whether the representative value for the first region of interest indicates respiration or motion of the subject involves identifying a second region of interest on the ratio surface related to a cardiac pulse frequency. A representative value is calculated for the second region of interest, and the representative value for the first region of interest is compared with the representative value for the second region of interest. The representative values for the first and second regions of interest may correspond to respective first and second functions. Comparing the representative value for the first region of interest with the representative value for the second region of interest may include, for example, comparing corresponding points on the first and second functions, respective median values of the first and second functions, respective average values of the first and second functions, or corresponding portions of the first and second functions. Similar representative values for the first and second regions of interest that are not near unity are indicative of baseline modulations in the first and second signals being more likely caused by respiration than movement.

In some embodiments, a pulse oximetry system includes an indicator, which may appear on display 28 of FIG. 1 or display 20 of FIG. 2, or any other display that is communicatively coupled to the pulse oximetry system, for indicating whether baseline modulation in at least one of the first and second respiration signal components (e.g., respiration signal components of red and IR wavelength components) is due to respiration or motion of the subject. The indicator may indicate that baseline modulation in at least one of the first and second respiration signal components is due to motion if the representative value of the first region of interest rises, as discussed further with respect to FIG. 15. In some embodiments, the indicator includes a visible or audible alarm that is triggered when a baseline modulation in at least one of the first and second respiration signal components is due to motion of the subject.

Figure 15:
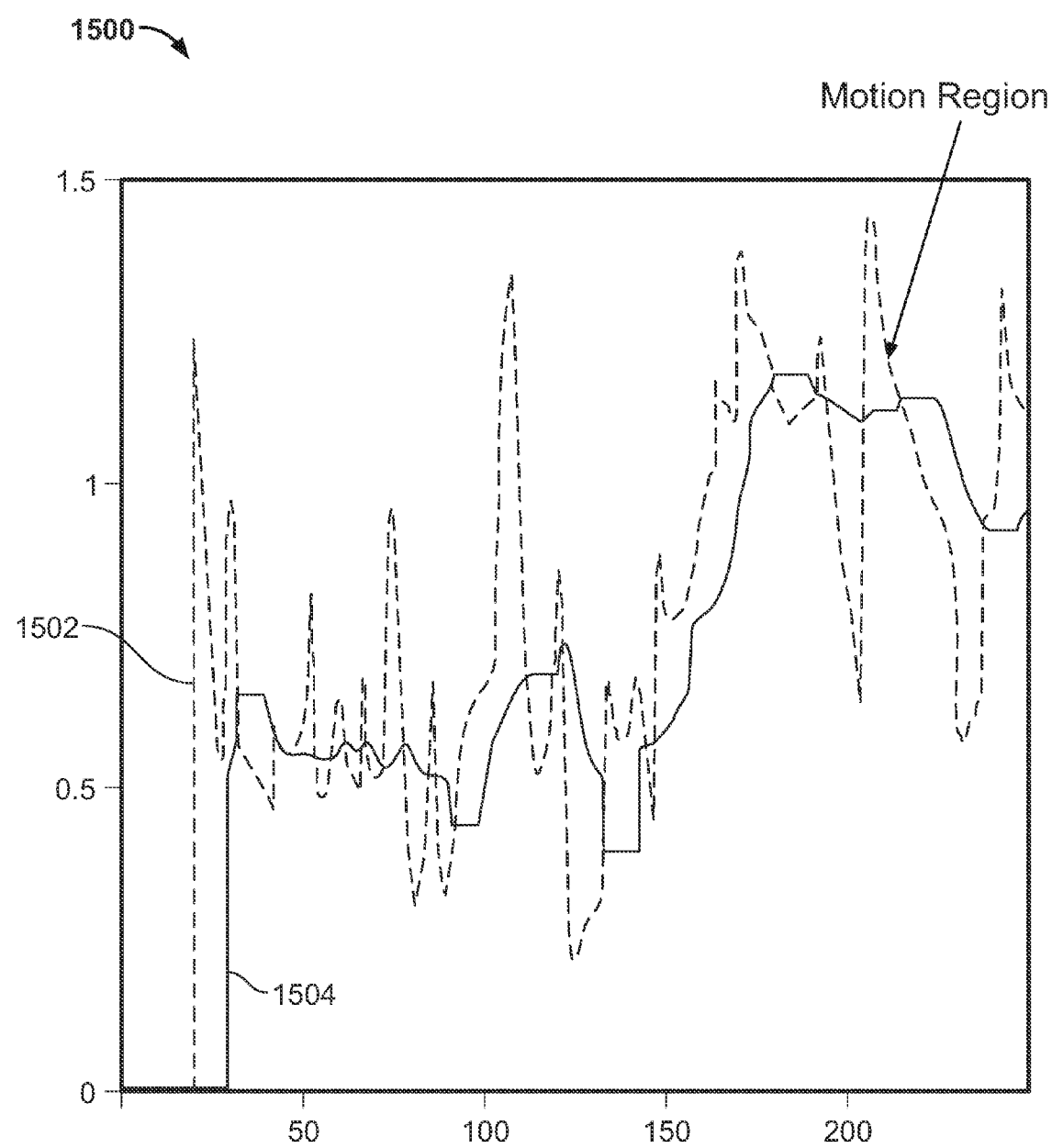
FIG. 15 shows an illustrative representative value of the illustrative ratio surface of FIG. 13 in accordance with some embodiments.

FIG. 15 shows a plot 1500 with an illustrative representative value 1504 of the illustrative ratio surface 1300 of FIG. 13 in the "respiration region" 1306 across time in accordance with some embodiments. The instantaneous ratio value across the band defined by lines 1302 and 1304 in FIG. 13 is shown by dashed line 1502 in plot 1500. Representative value 1504, shown as a continuous line in plot 1500, is the median value over a 20-second window of the mean value across the band. Other methods of filtering may be used instead of or in addition to this method of smoothing the instantaneous ratio value. The level of representative value 1504 rises distinctly due to the subject's motion, as indicated by the "Motion Region" label of plot 1500. In practice, such a change in the level of a representative value is considered to be an indication of motion artifact.

In some embodiments, multiple ridges are identified on and extracted from a ratio surface to determine which ridge is most likely due to respiration and which ridge is due to motion. The identification and extraction of multiple ridges may be particularly useful for low respiration rates which tend to have greater amplitude baseline signals and are harder to differentiate from some forms of motion. In some embodiments, identification and extraction of multiple ridges are used to detect potential low rate breathing and to adjust filter characteristics (e.g., cut-off ranges) in order to improve respiration rate calculation accuracy. In some embodiments, the ridges are extracted using methods discussed above in relation to FIGS. 12(*c*)-(*d*).

Figure 16:
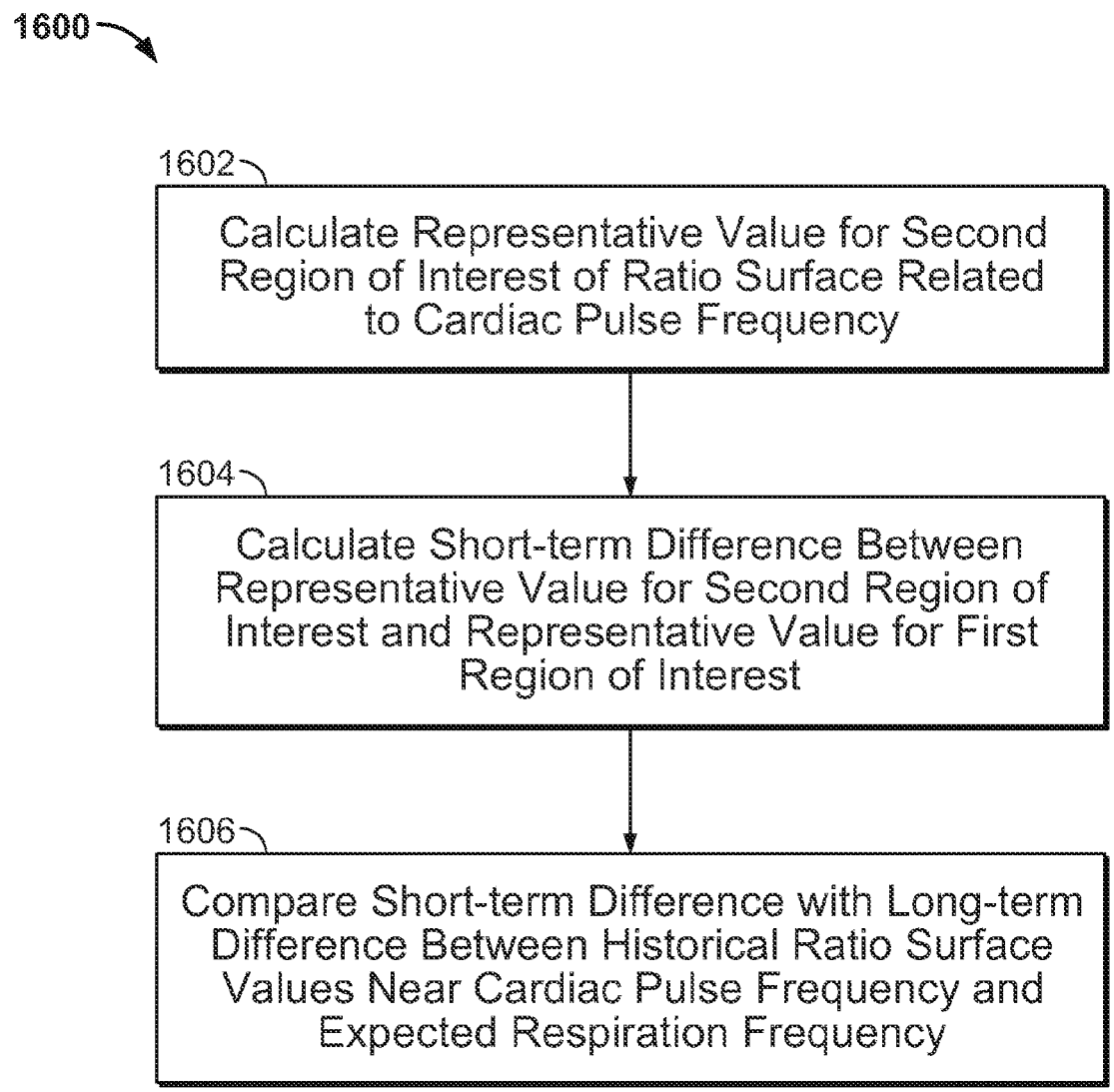
FIG. 16 is a flow chart of illustrative steps for analyzing a physiological signal obtained from a subject in accordance with some embodiments.

FIG. 16 is a flow chart 1600 of illustrative steps for analyzing a ratio surface with more than one region of interest to determine signal quality in accordance with some embodiments. FIG. 16 illustrates how to calculate a representative value for a second region of interest of a ratio surface (step 1602), and then how to calculate and use a short-term difference to determine signal quality (steps 1604 and 1606). The illustrative steps of flow chart 1600 may be performed as part of or in addition to the illustrative steps of flow chart 1400. The steps of flow chart 1600 may be performed by processing equipment such as processor 316 of FIG. 3, microprocessor 48 of FIG. 2, or any suitable processing device. The steps of flow chart 1600 may be performed by a digital processing device, or implemented in analog hardware. It will be noted that the steps of flow chart 1600 may be performed in any suitable order, and one or more steps may be omitted entirely according to the context and application.

At step 1602, a representative value is calculated for a second region of interest of a ratio surface related to a cardiac pulse frequency. The ratio surface may be derived at step 1408 of flow chart 1400. The representative value for the second region of interest may be calculated using the same method used at step 1412 to calculate the representative value for a first region of interest, or a different method may be used.

At step 1604, a short-term difference is calculated between the representative value for the second region of interest and the representative value for a first region of interest. The first region of interest may be identified at step 1410 of flow chart 1400. The representative value for the first region of interest may be calculated at step 1412 of flow chart 1400.

At step 1606, the short-term difference calculated at step 1604 is compared with a long-term difference between historical ratio surface values near the cardiac pulse frequency and an expected respiration frequency. Smaller deviations of the short-term difference from the long-term difference may indicate that baseline modulations in the first and second respiration signal components are due to respiration. Larger deviations of the short-term difference from the long-term difference may indicate that baseline modulations are due to motion.

In some embodiments, the long-term difference is a baseline finger oxygen usage measure. The finger oxygen usage measure may be expected to be relatively constant over time for baseline modulations that are due to respiration, even as arterial SpO2 changes. A physiological signal, such as a PPG signal, obtained at a subject's finger is useful for determining whether a modulation in the signal is due to respiration or movement, because the oxygen content of the arterial and venous blood at the finger may be very similar due to oxygen demand at the finger tip being relatively small. Any sudden deviations of a short-term difference from the established finger oxygen usage measure may indicate that modulations in the baseline region are due to the subject's motion. In other words, a short term finger oxygen usage measure that is similar to the long term average may indicate that recent modulations in the baseline region are likely due to the subject's respiration.

Cardiac Output

A venous oxygen saturation value determined with sufficient confidence (e.g., with adequate signal quality as determined by the steps described with respect to any of FIG. 6, 9-11, 14, or 16) can be used with a derived arterial oxygen saturation value to determine a patient's cardiac output. This calculation can be done, for example, using a Fick relationship. A representative Fick equation is:

$$Q = \frac{VO}{C_{aO2} - C_{vO2}} \tag{19}$$

Q is cardiac output, quantized as a flow rate of blood. VO is an oxygen consumption rate of a patient and may be quantized as units of oxygen per unit time. $C_{aO2}$ is concentration of oxygen in the arterial blood of the patient, ideally correlated to the oxygen content of oxygenated blood flowing from the heart. $C_{vO2}$ is concentration of oxygen in venous blood of the patient, ideally correlated to deoxygenated blood returning to the heart after circulating through the body. The term $(C_{aO2}-C_{vO2})$ represents a net oxygen concentration consumed by the patient's body, and is also known as the arteriovenous oxygen difference. It can be quantized as units of oxygen per unit volume. By dividing the consumption rate by concentration, a flow rate can be calculated, which corresponds to the cardiac output. Thus, given suitable parameters, the Fick equation can be used to accurately determine the cardiac output.

The Fick equation may be used to non-invasively determine cardiac output, if the parameters of VO and $(C_{aO2}-C_{vO2})$ can be measured non-invasively. In some embodiments, VO can be non-invasively measured by a ventilator fitted to a patient. Non-invasive techniques, such as photoplethysmography or any other suitable technique, may be used to determine $C_{aO2}$ and $C_{vO2}$, to enable an accurate and fully non-invasive method of determining cardiac output. The non-invasive techniques provided in the present disclosure are advantageous over conventional methods of measuring cardiac output, which require the insertion of at least two catheters into a sensitive parts of a subject to measure the oxygen content of arterial blood and venous blood. For example, the catheter used to measure venous blood may be placed in the vena cava, right atrium, right ventricle, or pulmonary artery. The catheter used to measure arterial blood may be placed in the aorta or a distal artery. Insertion of these catheters may be painful for the subject and require extended preparatory and recovery time.

Non-invasive methods of measuring cardiac output, such as rebreathing techniques (which estimate cardiac output via a modified Fick equation from a respiratory regime where part of the time the patient rebreathes carbon dioxide), transthoracic impedance, and bioreactance measurements (which correlate resistance and/or reactance to cardiac output), transthoracic Doppler ultrasound measurements (which compute the velocity of blood over a major vessel of known area from which flow may be computed), and pressure waveform analysis (which use non-invasively measured pressure waveforms at the finger which are correlated via a model to stroke volume and hence cardiac output) have been used in the past, but are not as convenient as the non-invasive techniques using Fick equations as discussed herein. The non-invasive techniques provided in the present disclosure are faster and more comfortable for patients than conventional invasive methods of measuring cardiac output, and may be more accurate than some other non-invasive techniques.

Figure 17:
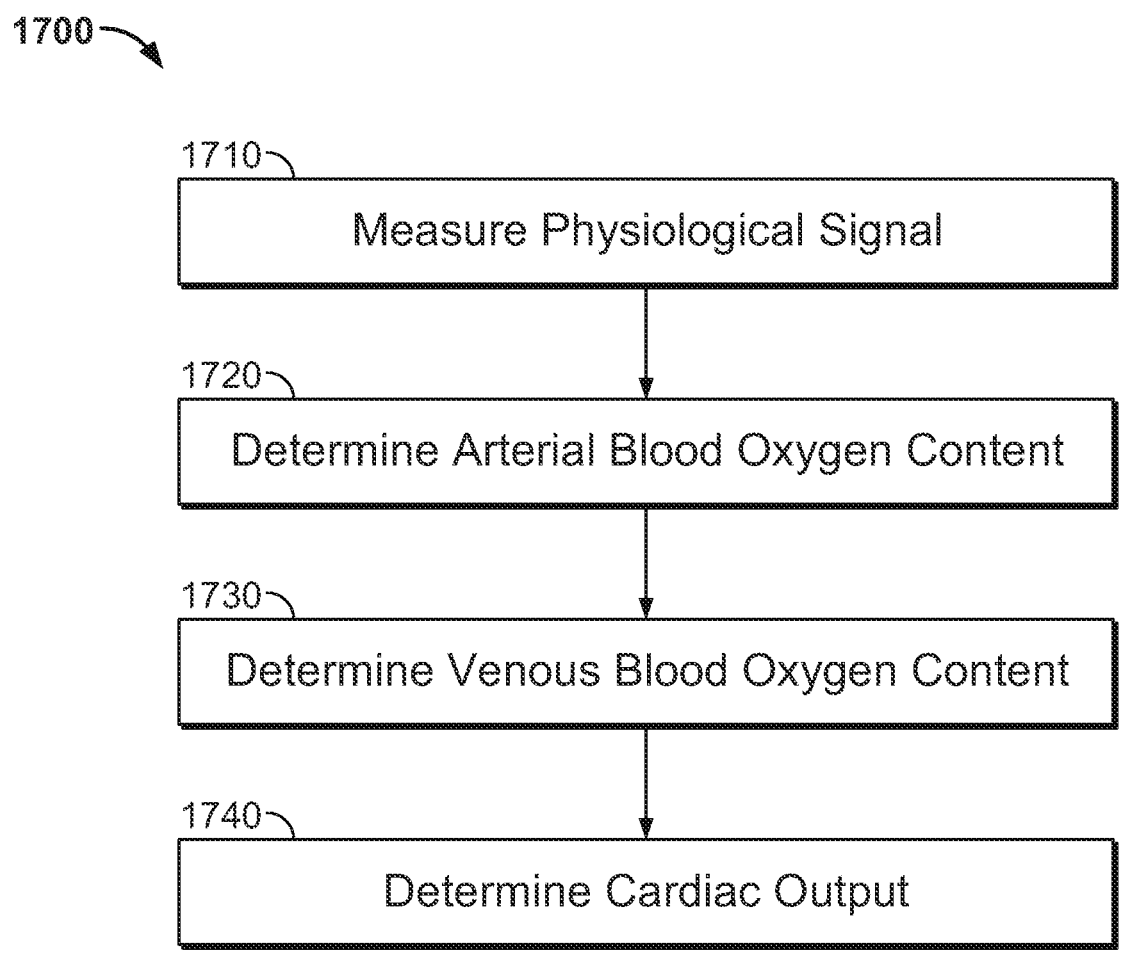
FIG. 17 is a flow chart of illustrative steps for non-invasively determining a cardiac output in accordance with some embodiments.

FIG. 17 is a flow chart 1700 of illustrative steps for non-invasively determining a cardiac output in accordance with some embodiments. FIG. 17 illustrates how to measure a signal (step 1710), how to determine arterial and venous blood oxygen content (steps 1720 and 1730), and how to determine cardiac output from the determined arterial and venous blood oxygen content (step 1740). The steps of flow chart 1700 may be performed by processing equipment such as processor 316 of FIG. 3, microprocessor 48 of FIG. 2, or any suitable processing device. The steps of flow chart 1700 may be performed by a digital processing device, or implemented in analog hardware. It will be noted that the steps of flow chart 1700 may be performed in any suitable order, and one or more steps may be omitted entirely according to the context and application.

In step 1710, a physiological signal is measured from a subject. The physiological signal may be a PPG signal or any other suitable signal. The physiological signal may include at least a first component indicative of arterial blood oxygen content and a second component indicative of venous return blood oxygen content. In some embodiments, the first component and second component are differentiated and separated in frequency, scale, or any other suitable indicator. For example, modulation of a PPG signal corresponding to an arterial component occurs at a higher frequency than modulation of a PPG signal corresponding to a venous component. Arterial modulation may be observed as a high frequency cardiac pulsatile component of a signal as shown in FIG. 4(a), in contrast to a low frequency baseline as shown in FIG. 4(b).

In step 1720, an arterial blood oxygen content is determined based at least in part on the first component indicative of arterial blood. The first component indicative of arterial blood may be a high frequency pulsatile component of a PPG signal comprising a red PPG signal and infrared PPG signal. An arterial blood oxygen saturation value may be determined by a ratio of ratios of the red PPG signal to the infrared PPG signal. This blood oxygen saturation (SpO2), which may be expressed as a percentage value, is used to determine the blood oxygen concentration by multiplying the SpO2 by a concentration of hemoglobin ($Hb_{conc}$) and by a term representing the oxygen carrying capacity of the hemoglobin. $Hb_{conc}$ may be quantized as units of mass per volume (g/mL). The oxygen carrying capacity of hemoglobin is about 1.34 mL of oxygen volume per gram of hemoglobin. Thus, the concentration of (bound) oxygen in the blood at a given oxygen saturation SpO2 may be expressed as:

$$C_{O2} = Hb_{conc} * 1.34 * SpO2 \text{ mL O2/dL} \tag{20}$$

$Hb_{conc}$ may be assumed to be a nominal value based on patient characteristics, measured by invasive means (such as a blood draw), or from a non-invasive measurement.

In step 1730, a venous blood oxygen content is determined based at least in part on the second component of the physiological signal indicative of venous blood. The second component indicative of venous blood may be a low frequency baseline component of a PPG signal comprising a red PPG signal and infrared PPG signal. The low frequency baseline component may be obtained by filtering the PPG signal around the breathing rate of the subject. A venous blood oxygen saturation may be determined from a ratio of ratios of the baseline red PPG and baseline infrared PPG. The venous blood oxygen saturation may be converted to a venous blood oxygen concentration using equation (20) described above, replacing SpO2 with the estimate of SvO2.

In step 1740, a cardiac output of the subject is determined based at least in part on the determined arterial blood oxygen content and determined venous blood oxygen content. In some embodiments, the Fick equation is used to determine the cardiac output using an arterial blood oxygen concentration and a venous blood oxygen concentration, as described in (19) above. If blood oxygen saturation values are measured instead of blood oxygen concentrations, the Fick equation may be modified to use blood oxygen saturation values as parameters.

$$Q = \frac{VO}{[(S_{aO2} - S_{vO2}) * Hb_{conc} * 1.34]} \quad (21)$$

For example, in some embodiments, a PPG measurement device as shown in FIG. 1 is connected to a subject. A PPG signal is measured from a signal probe on the subject's body. The signal may be filtered to separate the cardiac pulsatile component indicative of arterial blood, as shown in FIG. 4(*a*), from the baseline component indicative of venous blood, as shown in FIG. 4(*b*). Arterial blood oxygen saturation and venous blood oxygen saturation are then determined by computing a ratio of ratios of the red PPG and infrared PPG signals of the cardiac pulsatile and baseline components. An oxygen consumption rate may be determined by using a respirator, ventilator, or any other suitable measurement device that may be part of the PPG monitoring system or separate from the PPG monitoring system. The oxygen consumption rate and blood oxygen saturation values may be input to modified Fick equation (21) to calculate cardiac output.

The Fick equation calculates a flow rate by dividing a discharge rate by a concentration. The flow rate corresponds to the cardiac output, the discharge rate corresponds to the oxygen consumption rate, and the concentration corresponds to the arteriovenous difference as described in equation (19). Inaccuracies in the determination of the oxygen consumption rate or arteriovenous difference affect the accuracy of the determined cardiac output. In some embodiments, blood oxygen concentration parameterized in a Fick relationship is derived based in part on a PPG measurement. The PPG measurement analyzes the difference in absorption of IR and red light by hemoglobin in a subject's blood. Because the PPG measurement analyzes oxygen bound to hemoglobin, the PPG measurement may not detect oxygen that is dissolved in the blood plasma. The dissolved oxygen may be determined, given assumed or measured values of partial pressures of dissolved oxygen content in arterial and venous blood.

In some embodiments, a first physiological signal and a second physiological signal are measured from different parts of a patient's body to provide a stronger signal to noise ratio for arterial blood or venous blood respectively. Determination of cardiac output using the Fick method is most effective when the measure of arterial blood oxygen content correlates to blood leaving the heart, and when the measure of venous blood oxygen content correlates to blood entering the heart after circulating through the entire body, also known as venous blood.

Figure 18:
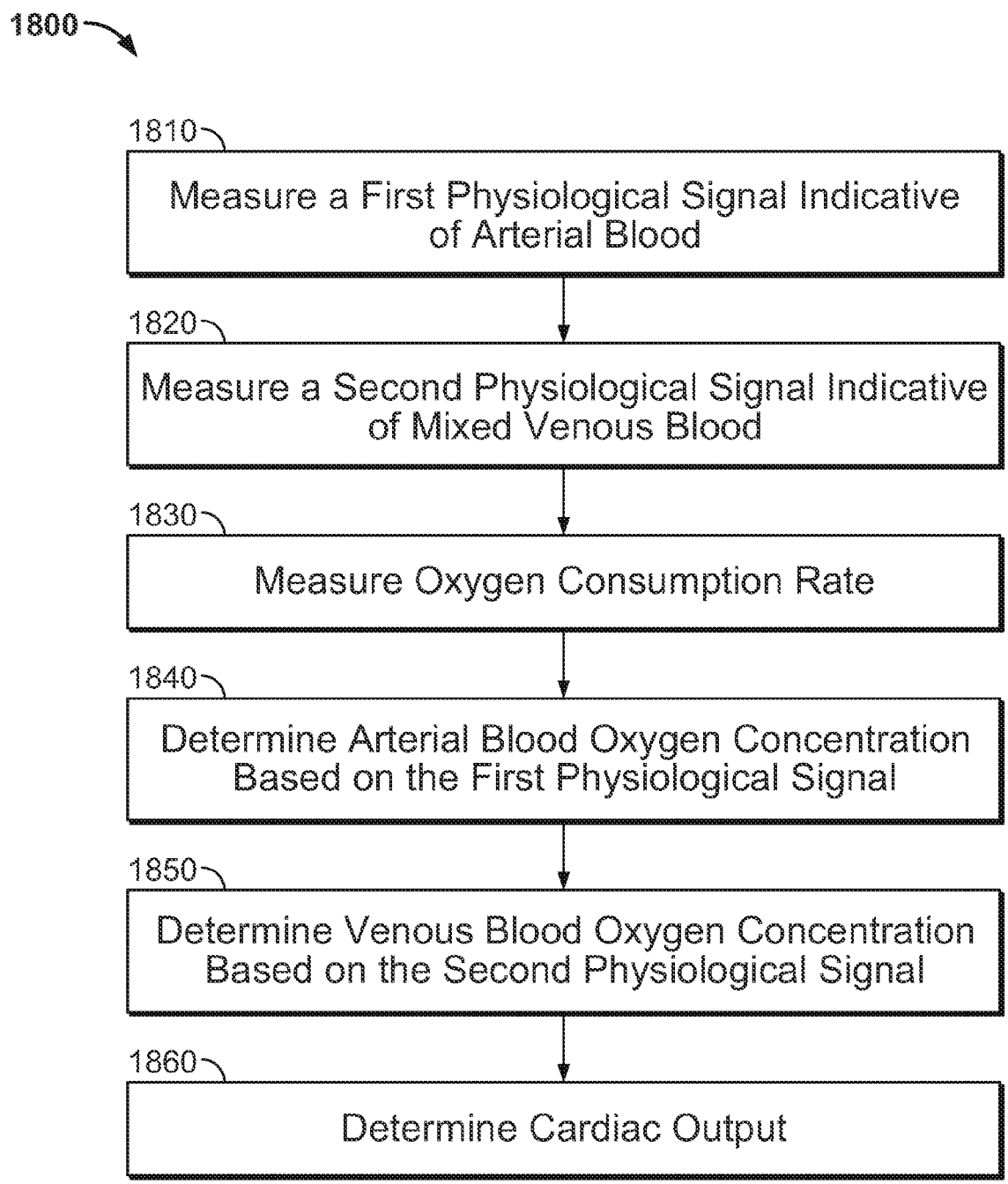
FIG. 18 is a flow chart of illustrative steps for non-invasively determining a cardiac output using a first measured physiological signal and a second measured physiological signal in accordance with some embodiments.

FIG. 18 is a flow chart 1800 of illustrative steps for non-invasively determining a cardiac output using a first measured physiological signal and a second measured physiological signal in accordance with some embodiments. FIG. 18 illustrates how to measure a first and second signal (steps 1810 and 1820), how to measure an oxygen consumption rate (step 1830), how to determine arterial and venous blood oxygen concentrations (steps 1840 and 1850), and then how to use the arterial and venous blood oxygen concentrations to determine a cardiac output (step 1860). The steps of flow chart 1800 may be performed as part of or in addition to the steps of flow chart 1700. The steps of flow chart 1800 may be performed by processing equipment such as processor 316 of FIG. 3, microprocessor 48 of FIG. 2, or any suitable processing device. The steps of flow chart 1800 may be performed by a digital processing device, or implemented in analog hardware. It will be noted that the steps of flow chart 1800 may be performed in any suitable order, and one or more steps may be omitted entirely according to the context and application.

In step 1810, a first physiological signal indicative of arterial blood is measured. In some embodiments, arterial blood oxygen content is measured using a PPG probe at the forehead, finger, chest, or any other suitable site, assuming that there is a negligible drop in blood oxygen saturation in the arterial blood en route to the peripheries.

In step 1820, a second physiological signal indicative of venous blood is measured. The second physiological signal may be measured using the same probe used to measure the first physiological signal, or measured using a different probe. The measurement of the second signal may be at the same site as the measurement of the first physiological signal, or at a second site different from the first.

The measurement of venous blood oxygen content is more constrained compared to the measurement of arterial blood oxygen content. Firstly, the venous measurement should be indicative of venous blood, which is representative of oxygen consumed during circulation of blood from the heart, through the body, and back to the heart. If venous return blood is not measured, then the determination of cardiac output may be inaccurate, at least because, depending on the measurement site chosen and the local blood flow relative to the local tissue's oxygen demand, a higher (or lower) SvO2 would be measured, leading to a lower (or higher) arteriovenous venous oxygen difference ($C_{aO2} - C_{vO2}$) and therefore a higher (or lower) than expected cardiac output. Secondly, measurement of venous blood by photoplethysmography is difficult because veins are usually located deep underneath the skin of a subject's body. In order to detect the blood in the veins, specialized probes having high sensitivity or measurement sites with veins close to the surface are required. For example, a PPG probe placed through the mouth into the esophagus near the chest cavity of a subject would provide a good measure of venous blood.

In step 1830, an oxygen consumption rate is measured. In some embodiments, the oxygen consumption rate is measured using a ventilator, respirator, or any other suitable measurement device. The measurement device for oxygen consumption may be part of a patient monitoring device, or may be a separate device that provides data that may be manually or automatically input into the patient monitoring device.

In step 1840, an arterial blood oxygen concentration based on the first physiological signal is determined. In some embodiments, this arterial blood oxygen concentration is determined from a blood oxygen saturation derived from a PPG signal. For example, a first component indicative of arterial blood may be a high frequency pulsatile component of a PPG signal comprising a red PPG signal and infrared PPG signal. An arterial blood oxygen saturation value may be determined from a ratio of ratios of the red PPG signal to the infrared PPG signal.

In step 1850, a venous blood oxygen concentration based on the second physiological signal is determined. In some embodiments, the venous blood oxygen concentration is determined from a blood oxygen saturation derived from a PPG signal. For example, a second component indicative of venous blood may be a baseline component of a PPG signal comprising a red PPG signal and infrared PPG signal. A venous blood oxygen saturation value may be determined from a ratio of ratios of the red PPG signal to the infrared PPG signal.

In step 1860, cardiac output is determined by using a Fick equation. In some embodiments, blood oxygen saturation values are measured and input into a modified Fick equation, described by equation (21), to determine the cardiac output.

To more accurately determine a cardiac output using Fick's equation, the Fick equation may be modified to account for dissolved oxygen by adding a term indicative of dissolved oxygen. Indicators of dissolved oxygen may include partial pressure, spectral absorbance, or any other suitable indicator. In some embodiments, the blood oxygen content may be modified by adding a term indicative of partial pressure. According to the ideal gas law, provided below in equation (22), pressure directly correlates with the number of moles of oxygen, P is pressure, V is volume, n is a number of moles, R is an ideal gas constant, and T is a temperature:

$$PV = nRT \tag{22}$$

By dividing both sides by volume, the pressure P is directly proportional to a molar concentration (n/V). Ideal gas analysis applies to a pure gaseous phase, but also correlates to dissolved gases within a solution. Ideal gas analysis relates partial pressure to dissolved gas content.

$$P = \frac{n}{V}RT \tag{23}$$

As an example, the Fick Equation may be modified by adding a partial pressure term indicative of dissolved gases:

$$Q = \frac{VO}{[(S_{aO2} - S_{vO2}) * Hb_{conc} * 1.34] + [P_{aO2} - P_{vO2}] * K} \tag{24}$$

The partial pressure term is $(P_{aO2} - P_{vO2})*K$, where K is a constant to convert from pressure to concentration and may account for temperature, fluid properties, or any other suitable environmental factors. In practice the value of –0.003 is often used for the constant K.

Figure 19:
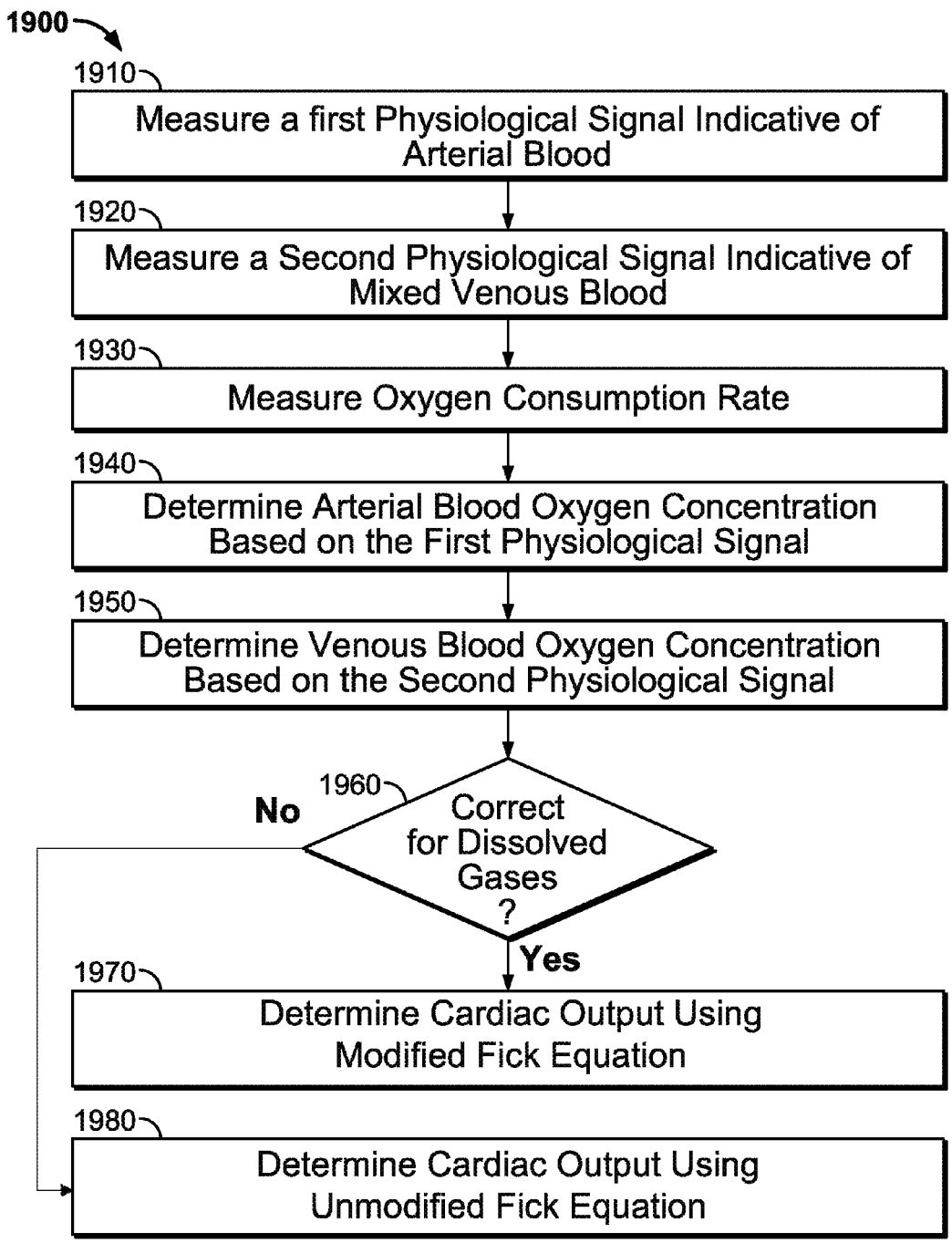
FIG. 19 is a flow chart of illustrative steps for non-invasively determining a cardiac output and correcting for dissolved gases in accordance with some embodiments.

FIG. 19 is a flow chart 1900 of illustrative steps for non-invasively determining a cardiac output and correcting for dissolved gases in accordance with some embodiments. FIG. 19 illustrates how to measure a first and second signal (steps 1910 and 1920), how to measure an oxygen consumption rate (step 1930), how to determine arterial and venous blood oxygen concentrations (steps 1940 and 1950), and then how to correct for dissolved gases to determine a cardiac output (steps 1960, 1970, 1980, and 1990). The steps of flow chart 1900 may be performed as part of or in addition to the steps of flow chart 1700 or 1800. The steps of flow chart 1900 may be performed by processing equipment such as processor 316 of FIG. 3, microprocessor 48 of FIG. 2, or any suitable processing device. The steps of flow chart 1900 may be performed by a digital processing device or implemented in analog hardware. It will be noted that the steps of flow chart 1900 may be performed in any suitable order, and one or more steps may be omitted entirely according to the context and application.

In step 1910, a first physiological signal indicative of arterial blood is measured. The first physiological signal may be a PPG signal or any other suitable signal. In some embodiments, the first physiological signal may be a PPG signal comprising a red PPG signal component and infrared PPG signal component. For example, the PPG signal components may correspond to a high frequency cardiac pulsatile component indicative of arterial blood, as illustrated in FIG. 4(*a*).

In step 1920, a second physiological signal indicative of venous return blood is measured. The second physiological signal may be a PPG signal or any other suitable signal. In some embodiments, the second physiological signal is a PPG signal comprising a red PPG signal component and infrared PPG signal component. For example, the PPG signal components may correspond to a low frequency baseline component indicative of venous blood, as illustrated in FIG. 4(*b*). The second physiological signal may be measured using the same probe used to measure the first signal, or a second probe different from the first probe. The second signal may be measured at the same site on the patient as the first probe, or at a second site. In some embodiments, the second physiological signal is measured at a site indicative of venous blood return. For example, the second physiological signal may be a signal measured from a PPG probe placed in the mouth through the esophagus into the chest cavity of the patient.

In step 1930, an oxygen consumption rate is measured. The oxygen consumption rate may be measured by a ventilator, respirator, or any other suitable measurement device.

In step 1940, arterial blood oxygen concentration is determined based in part on the first physiological signal. In some embodiments, the blood oxygen concentration is determined from a blood oxygen saturation derived from a PPG signal. For example, equation (20) may be used to relate the blood oxygen saturation to the blood oxygen concentration.

In step 1950, venous blood oxygen concentration is determined based in part on the second physiological signal. In some embodiments, the blood oxygen concentration is determined from a blood oxygen saturation derived from a PPG signal. For example, equation (20) may be used to relate the blood oxygen saturation to the blood oxygen concentration.

In step 1960, a determination is made whether to correct for dissolved gases. This determination may be made by processor 312 in FIG. 3, microprocessor 48 in FIG. 2, or any other suitable processing equipment. The determination may be made in response to user inputs 56 or stored settings in ROM 52 or RAM 54 in FIG. 2, or any other suitable storage equipment. If there is a determination to correct for dissolved gases, the next step will be step 1970, determination of the cardiac output using the modified Fick equation. If there is a determination not to correct for dissolved gases, the next step will be step 1980, determination of cardiac output using the unmodified Fick equation.

The above described embodiments of the present disclosure are presented for purposes of illustration and not of limitation, and the present disclosure is limited only by the claims which follow.

The invention claimed is:

1. A method for determining a respiration rate of a subject, the method comprising:
transforming, using a signal processor, a first physiological signal based on light transmission at a first wavelength to generate a first transformed signal;
transforming, using the signal processor, a second physiological signal based on light transmission at a second wavelength to generate a second transformed signal;
deriving, using the signal processor, a ratio surface from the first transformed signal and the second transformed signal, wherein the ratio surface comprises three-dimensional data with dimensions including time and scale;
identifying, using the signal processor, a first region of interest on the ratio surface indicative of venous perturbation;
calculating, using the signal processor, a representative value for the first region of interest on the ratio surface;
making, using the signal processor, a determination as to whether the calculated representative value for the first region of interest indicates respiration or motion of the subject based on the calculated representative value, wherein determining whether the representative value for the first region of interest indicates respiration or motion of the subject comprises:
calculating a representative value for a second region of interest of the ratio surface related to a cardiac pulse frequency;
calculating a short-term difference between the representative value for the second region of interest and the representative value for the first region of interest; and
comparing the short-term difference with a long-term difference between historical ratio surface values near the cardiac pulse frequency and an expected respiration frequency, wherein smaller deviations of the short-term difference from the long-term difference are indicative of baseline modulations in the first and second signals being due to respiration, and larger deviations of the short-term difference from the long-term difference are indicative of baseline modulations being due to motion; and
calculating, using the signal processor, the respiration rate of the subject when the calculated representative value for the first region of interest indicates respiration.

2. The method of claim 1, further comprising:
identifying areas of the ratio surface having values close to an expected venous saturation ratio value; and
computing an estimated rate of respiration of the subject based on the identified areas.

3. The method of claim 1, wherein deriving the ratio surface comprises normalizing the first and second physiological signals.

4. The method of claim 3, wherein the normalizing comprises dividing the respective magnitude of each of the first and second physiological signals by the respective minimum, maximum, mean, DC component, or standard deviation computed over a time window of the first and second physiological signals.

5. The method of claim 1, wherein transforming the first and second signal comprises using a wavelet transform.

6. The method of claim 5, wherein transforming of the first and second signal comprises applying the wavelet transform to derivatives of the first and second signals.

7. The method of claim 5, wherein deriving the ratio surface comprises:
calculating a first modulus of the transform of the first signal;
calculating a second modulus of the transform of the second signal; and
dividing the first modulus by the second modulus.

8. The method of claim 5, wherein calculating the representative value comprises filtering instantaneous values of the ratio surface.

9. The method of claim 8, wherein the filtering comprises calculating a median value over a specified time interval of a mean value across the first region of interest.

10. The method of claim 1, wherein the first region of interest includes a characteristic frequency at which respiration occurs.

11. A system for determining a respiration rate of a subject, the system comprising:
a signal input configured to receive a physiological signal of the subject from a sensing device; and
one or more processing devices in communication with the signal input and configured to:
transform a first physiological signal based on light transmission at a first wavelength to generate a first transformed signal;
transform a second physiological signal based on light transmission at a second wavelength to generate a second transformed signal;
derive a ratio surface from the first transformed signal and the second transformed signal, wherein the ratio surface comprises three-dimensional data with dimensions including at least time and scale;
calculate a representative value for a first region of interest on the ratio surface, wherein the first region of interest is related to a respiration rate;
determine whether baseline modulation in at least one of the first and second signals is due to respiration of the subject based on the calculated representative value, wherein the determining comprises:
calculating a representative value for a second region of interest of the ratio surface related to a cardiac pulse frequency;
calculating a short-term difference between the representative value for the second region of interest and the representative value for the first region of interest; and
comparing the short-term difference with a long-term difference between historical ratio surface values near the cardiac pulse frequency and an expected respiration frequency, wherein:
the indicator will indicate that baseline modulation in at least one of the first and second signals is due to respiration of the subject when there are small deviations of the short-term difference from the long-term difference, and the indicator will indicate that baseline modulation in at least one of the first and second signals is due to motion of the subject when there are large deviations of the short-term difference from the long-term difference; and
calculate the respiration rate of the subject based on the determination.

12. The system of claim 11, wherein the one or more processing devices are further configured to transform the first and second signals using a wavelet transform.

13. The system of claim 12, wherein the one or more processing devices are further configured to:
calculate a first modulus of the transform of the first signal;

calculate a second modulus of the transform of the second signal; and divide the first modulus by the second modulus.

14. The system of claim 11, wherein the first region of interest includes a frequency at which respiration occurs.

15. The system of claim 11, further comprising an indicator for indicating whether baseline modulation in at least one of the first and second signals is due to respiration or motion of the subject.

16. The system of claim 15, wherein the indicator comprises an alarm that is triggered when baseline modulation in at least one of the first and second signal is due to motion of the subject.

17. The system of claim 11, wherein the one or more processing devices are further configured to:

identify areas of the ratio surface having values close to an expected venous saturation ratio value; and compute an estimated rate of respiration of the subject based on the identified areas.

* * * * *